United States Patent [19]
Deo et al.

[11] Patent Number: 5,922,845
[45] Date of Patent: Jul. 13, 1999

[54] THERAPEUTIC MULTISPECIFIC COMPOUNDS COMPRISED OF ANTI-FCα RECEPTOR ANTIBODIES

[75] Inventors: Yashwant M. Deo, Audubon, Pa.; Robert Graziano, Frenchtown, N.J.; Tibor Keler, Ottsville, Pa.

[73] Assignee: Medarex, Inc., Annandale, N.J.

[21] Appl. No.: 08/678,194

[22] Filed: Jul. 11, 1996

[51] Int. Cl.$^6$ .......................... C12P 21/08; C07K 16/28; C07K 19/00; A61K 39/395

[52] U.S. Cl. ................... 530/387.3; 530/395; 530/388.1; 424/136.1; 424/184.1; 424/204.1; 424/234.1; 424/265.1; 424/274.1; 424/277.1; 536/23.5; 435/69.7

[58] Field of Search .................................. 530/387.3, 395, 530/388.1; 424/136.1, 184.1, 204.1, 234.1, 265.1, 274.1, 277.1; 435/69.7; 536/23.5

[56] References Cited

FOREIGN PATENT DOCUMENTS

| | | |
|---|---|---|
| 0 255 249 | 2/1988 | European Pat. Off. |
| WO 91/00360 | 1/1991 | WIPO. |
| WO 91/05805 | 5/1991 | WIPO. |
| WO 92/05793 | 4/1992 | WIPO. |
| WO 94/08038 | 4/1994 | WIPO. |
| WO 95/16037 | 6/1995 | WIPO. |
| WO 95/24220 | 9/1995 | WIPO. |
| WO 96/40788 | 12/1996 | WIPO. |

OTHER PUBLICATIONS

Deo, Y.M. et al. (1997) "Fcα directed bispecific molecules (BSM) mediate lysis and phagocytosis of tumor cells" *Proceedings of the American Association For Cancer Research* 38: 30, Abstract No. 195.

Fanger, M.W. et al. (1994) "Production and use of anti–fcr bispecific antibodies" *Immunomethods* 4: 72–81.

Kettleborough, C.A. et al. (1991) "Humanization of a mouse monoclonal antibody by CDR–grafting: the importance of framework residues on loop conformation" *Protein Engineering* 4(7): 773–783.

McCall, A.M. et al. (1996) "Production of bispecific single–chain Fvs (sFv')$_2$ specific for the oncogene product c–erbB–2 and human CD16/mouse FcγRII/III using recombinant phage display libraries" *Proceedings of the American Association For Cancer Research* 37: 472, Abstract No. 3218.

Weiner, L.M. et al. (1995) "Phase I trial of 2B1, a bispecific monoclonal antibody targeting c–erbB–2 and FcγRIII" *Cancer Research* 55: 4586–4593.

Sandhu (J.S.) 1992 Critical Reviews in BioTechnology vol. 12 (5,6) 1992 pp. 437–462.

Alkan, S. et al., "Enhanced Antiproliferative Action of Interferon Targeted by Bispecific Monoclonal Antibodies," *Journal of Interferon Research*, vol. 8, 25–33 (1988).

Bacus, S. et al., "Expression of the erbB–2 Family of Growth Factor Receptors and their Ligands in Breast Cancers," *Am J Clin Pathol*, vol. 102, supp. 1, S13–S24 (1994).

Bajorath, J. and Sheriff, S., "Comparison of an Antibody Model with an X–Ray Structure: The Variable Fragment of BR96," *Proteins: Structure, Function, and Genetics*, vol. 24, 152–157 (1996).

De Potter, C. and Schelfhout, A., "The Neu–Protein and Breast Cancer," *Virchows Archiv*, vol. 426, 107–115 (1995).

Devilee, P. et al., "Recent Developments in the Molecular Genetic Understanding of Breast Cancer," *Critical Reviews in Oncogenesis*, vol. 5, No. 2 & 3, 247–270 (1994).

Earp, H. et al., "Heterodimerization and Functional Interaction Between EGF Receptor Family Members: A New Signaling Paradigm with Implications for Breast Cancer Research," *Breast Cancer Research and Treatment*, vol. 35, 115–132 (1995).

Grossetête, B. et al., "Impaired Fcα Receptor Expression is Linked to Increased Immunoglobulin A Levels and Disease Progression in HIV–1–Infected Patients," *AIDS*, vol. 9, 229–234 (1995).

Jardines, L. et al., "neu(c–erbB–2/HER2) and the Epidermal Growth Factor Receptor (EGFR) in Breast Cancer," *Pathobiology*, vol. 61, 268–282 (1993).

Johnson, G. et al., "Seqhunt: A Program to Screen Aligned Nucleotide and Amino Acid Sequences," *Methods in Molecular Biology*, vol. 51, ch. 1, 1–15 (1995).

(List continued on next page.)

*Primary Examiner*—Toni R. Scheiner
*Assistant Examiner*—Geetha P. Bansal
*Attorney, Agent, or Firm*—Lahive & Cockfield, LLP; Giulio A. DeConiti, Jr.; Jane E. Remillard

[57] ABSTRACT

Therapeutic multispecific compounds comprised of anti-Fcα receptor antibodies and methods of use are provided.

24 Claims, 15 Drawing Sheets

OTHER PUBLICATIONS

Keler, T. et al., "Bispecific Antibody (MDX–210) Targeting of Tumor Cells to Monocytes Via the Fc Receptor Type I (FcγRI) Promotes Antibody Dependent Cellular Cytotoxicity (ADCC) and Induction of Specific Cytokines," *Proceedings of the American Association for Cancer Research*, vol. 36, 485 (1995).

Kubagawa, H. et al., "Cloning of Genes Encoding Possible Murine Fcα Receptors (FcαR)," *FASEB J.*, vol. 8, No. 4–5, A749 (1994).

Mezzanzanica, D. et al., "Human Ovarian Carcinoma Lysis by Cytotoxic T Cells Targeted by Bispecific Monoclonal Antibodies: Analysis of the Antibody Components," *Int. J. Cancer*, vol. 41, 609–615 (1988).

Monteiro, R. et al., "Definition of Immunoglobulin A Receptors on Eosinophils and their Enhanced Expression in Allergic Individuals," *J. Clin. Invest.*, vol. 92, 1681–1685 (1993).

Monteiro, R. et al., "Molecular Heterogeneity of Fcα Receptors Detected by Receptor–Specific Monoclonal Antibodies," *The Journal of Immunology*, vol. 148, No. 6, 1764–1770 (1992).

Patry, C. et al., "Fcα Receptors Mediate Release of Tumour Necrosis Factor–α and Interleukin–6 by Human Monocytes Following Receptor Aggregation," *Immunology*, vol. 86, 1–5 (1995).

Patry, C. et al., "Identification of Fcα Receptor (CD89) Isoforms Generated by Alternative Splicing that are Differentially Expressed Between Blood Monocytes and Alveolar Macrophages," *The Journal of immunology*, vol. 156, 4442–4448 (1996).

Pfefferkorn, L. and Yeaman, G., "Association of IgA–Fc Receptors (FcαR) with FcεRIγ2 Subunits in U937 Cells," *The Journal of immunology*, vol. 153, 3228–3236 (1994).

Shimada, T. et al., "Comparative Analysis of FcαR on Neutrophils and Monocytes," *FASEB J.*, vol. 9, No. 4, A804 (1995).

Shimo, K. et al., "Ligand–Binding Properties of Recombinant Soluble Fcα Receptor," *FASEB J.*, vol. 9, No. 4, A774 (1995).

Threlkeld, S.C. et al., "Differential Down–Modulation of IgA Fc Receptors (FcαR) on Neutrophils and Monocytes in HIV–Infected and Normal Individuals," *FASEB J.*, vol. 8, No. 4–5, A492 (1994).

Valone, F. et al., "Phase Ia/Ib Trial of Bispecific Antibody MDX–210 in Patients with Advanced Breast or Ovarian Cancer that Overexpresses the Proto–Oncogene HER–2/neu," *J Clin Oncol*, vol. 13, No. 9, 2281–2292 (1995).

Valone, F.H. et al., "Schedule Dependent Immunological Stimulation by Bispecific Antibody (BsAb) MDX–210 (anti–FcγRI×anti–HER–2/neu) in Patients with Breast or Ovarian Cancers that Over Express HER–2/neu," *Proceedings of the American Association for Cancer Research*, vol. 36, 500 (1995).

Webster, D. and Rees, A., "Molecular Modeling of Antibody–Combining Sites," *Methods in Molecular Biology*, vol. 51, 17–49 (1995).

Weisbart, R.H. et al., "GM–CSF Induces Human Neutrophil IgA–Mediated Phagocytosis by an IgA Fc Receptor Activation Mechanism," *Nature*, vol. 332, 647–648 (1988).

Yeaman, G. and Pfefferkorn, L.C., "IgA–Fc Receptors (FcαR) on U937 Cells Associate with FcεRI Gamma Subunits," *FASEB J.*, vol. 8, No. 4–5, A981 (1994).

Sequence Range: 1 to 336

```
              10            20            30            40
          *    *     *    *     *    *     *    *     *
        GAC  ATT  CAG  CTG  ACC  CAG  TCT  CCA  CTC  ACT  TTG  TCG  ATT  ACC  ATT  GGA
        CTG  TAA  GTC  GAC  TGG  GTC  AGA  GGT  GAG  TGA  AAC  AGC  TAA  TGG  TAA  CCT
        Asp  Ile  Gln  Leu  Thr  Gln  Ser  Pro  Leu  Thr  Leu  Ser  Ile  Thr  Ile  Gly>

50            60            70            80            90
    *    *     *    *     *    *     *    *     *    *
   CAA  CCA  GCC  TCC  ATC  TCT  TGC  AAG  TCA  AGT  CAG  AGC  CTC  TTA  GAT  AGT
   GTT  GGT  CGG  AGG  TAG  AGA  ACG  TTC  AGT  TCA  GTC  TCG  GAG  AAT  CTA  TCA
   Gln  Pro  Ala  Ser  Ile  Ser  Cys  Lys  Ser  Ser  Gln  Ser  Leu  Leu  Asp  Ser>

100           110           120           130           140
        *    *     *    *     *    *     *    *     *
       GAT  GGA  AAG  ACA  TAT  TTG  AAT  TGG  TTG  TTA  CAG  AGG  CCA  GGC  CAG  TCT
       CTA  CCT  TTC  TGT  ATA  AAC  TTA  ACC  AAC  AAT  GTC  TCC  GGT  CCG  GTC  AGA
       Asp  Gly  Lys  Thr  Tyr  Leu  Asn  Trp  Leu  Leu  Gln  Arg  Pro  Gly  Gln  Ser>

150           160           170           180           190
    *    *     *    *     *    *     *    *     *    *
   CCA  ACG  CGC  CTA  ATC  TAT  CTG  GTG  TCT  AAA  CTG  GAC  TCT  GGA  GTC  CCT
   GGT  TGC  GCG  GAT  TAG  ATA  GAC  CAC  AGA  TTT  GAC  CTG  AGA  CCT  CAG  GGA
   Pro  Thr  Arg  Leu  Ile  Tyr  Leu  Val  Ser  Lys  Leu  Asp  Ser  Gly  Val  Pro>

200           210           220           230           240
        *    *     *    *     *    *     *    *     *    *
       GAC  AGG  TTC  ACT  GGC  AGT  GGA  TCA  GGG  ACA  GAT  TTC  ACA  CTG  AAA  ATC
       CTG  TCC  AAG  TGA  CCG  TCA  CCT  AGT  CCC  TGT  CTA  AAG  TGT  GAC  TTT  TAG
       Asp  Arg  Phe  Thr  Gly  Ser  Gly  Ser  Gly  Thr  Asp  Phe  Thr  Leu  Lys  Ile>

250           260           270           280
        *    *     *    *     *    *     *    *     *
       AGC  AGA  GTG  GAG  GCT  GAG  GAT  TTG  GGA  ATT  TAT  TAT  TGC  TGG  CAA  GGT
       TCG  TCT  CAC  CTC  CGA  CTC  CTA  AAC  CCT  TAA  ATA  ATA  ACG  ACC  GTT  CCA
       Ser  Arg  Val  Glu  Ala  Glu  Asp  Leu  Gly  Ile  Tyr  Tyr  Cys  Trp  Gln  Gly>

290           300           310           320           330
    *    *     *    *     *    *     *    *     *    *
   GCA  CAT  TTT  CCT  CAG  ACG  TTC  GGT  GGA  GGC  ACC  AAG  CTG  GAA  ATC  AAA
   CGT  GTA  AAA  GGA  GTC  TGC  AAG  CCA  CCT  CCG  TGG  TTC  GAC  CTT  TAG  TTT
   Ala  His  Phe  Pro  Gln  Thr  Phe  Gly  Gly  Gly  Thr  Lys  Leu  Glu  Ile  Lys>
```

Fig. 14

Sequence Range: 1 to 426

```
          10            20            30            40
           *             *             *             *        *
ATG GGA TGG AGC TGG GTC ATT ATC TTC CTC CTG TCA GGA ACT GCA GGA
TAC CCT ACC TCG ACC CAG TAA TAG AAG GAG GAC AGT CCT TGA CGT CCT
Met Gly Trp Ser Trp Val Ile Ile Phe Leu Leu Ser Gly Thr Ala Gly>

50            60            70            80            90
  *             *       *     *             *       *     *        *
GCC CAC TCT GAG ATC CAG CTG CAG CAG ACT GGA CCT GAG CTG GTG AAG
CGG GTG AGA CTC TAG GTC GAC GTC GTC TGA CCT GGA CTC GAC CAC TTC
Ala His Ser Glu Ile Gln Leu Gln Gln Thr Gly Pro Glu Leu Val Lys>

100           110           120           130           140
     *     *       *       *     *       *     *       *     *
CCT GGG GCT TCA GTG AAG ATA TCC TGC AAG GCT TCT GGT TAT TCA TTC
GGA CCC CGA AGT CAC TTC TAT AGG ACG TTC CGA AGA CCA ATA AGT AAG
Pro Gly Ala Ser Val Lys Ile Ser Cys Lys Ala Ser Gly Tyr Ser Phe>

150           160           170           180           190
  .      *      *       *       *      *      *      *      *      *
ACT GAC TAC ATC ATA TTT TGG GTG AAG CAG AGC CAT GGA AAG AGC CTT
TGA CTG ATG TAG TAT AAA ACC CAC TTC GTC TCG GTA CCT TTC TCG GAA
Thr Asp Tyr Ile Ile Phe Trp Val Lys Gln Ser His Gly Lys Ser Leu>

200           210           220           230           240
            *       *     *      *       *     *       *     *      *
GAG TGG ACT GGA AAT ATT AAT CCT TAC TAT GGT AGT ACT AGC TAC AAT
CTC ACC TGA CCT TTA TAA TTA GGA ATG ATA CCA TCA TGA TCG ATG TTA
Glu Trp Thr Gly Asn Ile Asn Pro Tyr Tyr Gly Ser Thr Ser Tyr Asn>

250           260           270           280
               *      *       *       *       *      *       *     *
CTG AAG TTC AAG GGC AAG GCC ACA TTG ACT GTA GAC AAA TCT TCC AGC
GAC TTC AAG TTC CCG TTC CGG TGT AAC TGA CAT CTG TTT AGA AGG TCG
Leu Lys Phe Lys Gly Lys Ala Thr Leu Thr Val Asp Lys Ser Ser Ser>

290           300           310           320           330
 *       *     *       *     *       *     *       *     *        *
ACA GCC TAC ATG CAG CTC AAC AGT CTG ACA TCT GAG GAC TCT GCA GTC
TGT CGG ATG TAC GTC GAG TTG TCA GAC TGT AGA CTC CTG AGA CGT CAG
Thr Ala Tyr Met Gln Leu Asn Ser Leu Thr Ser Glu Asp Ser Ala Val>

340           350           360           370           380
     *      *       *       *     *       *     *       *     *
TAT TAC TGT GTA AGA GGA GTT TAT TAC TAC GGT AGT AGC TAC GAG GCG
ATA ATG ACA CAT TCT CCT CAA ATA ATG ATG CCA TCA TCG ATG CTC CGC
Tyr Tyr Cys Val Arg Gly Val Tyr Tyr Tyr Gly Ser Ser Tyr Glu Ala>

390           400           410           420
  *      *       *       *     *       *     *       *      *
TTT CCT TAC TGG GGC CAA GGG ACT CTG GTC ACT GTC TCT GCA
AAA GGA ATG ACC CCG GTT CCC TGA GAC CAG TGA CAG AGA CGT
Phe Pro Tyr Trp Gly Gln Gly Thr Leu Val Thr Val Ser Ala>
```

Fig. 15

THERAPEUTIC MULTISPECIFIC COMPOUNDS COMPRISED OF ANTI-FCα RECEPTOR ANTIBODIES

BACKGROUND OF THE INVENTION

Receptors for the Fc portions of immunoglobulins are important in triggering many of the protective functions of monocytes, macrophages and polymorphonuclear cells. Receptors for IgG (Fcγ receptors or FcγR) on these cells have been extensively investigated and bispecific molecules targeting these receptors have been constructed. (See e.g. European Patent No. 0 255 249 entitled "Monoclonal Antibodies to Fc Receptor for Immunoglobulin G on Human Mononuclear Phagocytes", which is co-owned by Applicants.) In addition, clinical trials of bispecific molecules which have specificity for the FcγR and the HER-2/neu antigen, which is found on breast or ovarian cancers, indicate that these molecules are both safe and efficacious (Valone, Frank H. et al. 1995, *J of Clin. Oncol.* 13(9): 2281–2292).

IgA receptors Fcα receptors (FcαR or CD89) are also capable of promoting effector cell function. Binding of ligand to FcαR triggers phagocytosis and and antibody mediated cell cytotoxicity in leukocytes and FcαR-bearing cell lines. Fcα receptors can also cooperate with receptors for IgG on effector cells in enhancing the phagocytosis of target cells. Monoclonal antibodies of the IgM (Shen, L. et al., 1989 *J Immunol.* 143: 4117) and IgG (Monteiro, R. C. et al., 1992 *J Immunol,* 148: 1764) classes have been developed against FcαR.

SUMMARY OF THE INVENTION

In general, the present invention relates to multispecific therapeutic molecules with binding determinants for immunoglobulin A (IgA) receptors. IgA is the predominant antibody class in fluids on mucosal surfaces, and IgA receptors (Fcα receptors, or FcαR) are found on white blood cells including macrophages, monocytes, neutrophils, eosinophils and lymphocytes. The bispecific and multispecific molecules of the invention can be used as therapeutic agents to harness the cytolysis and phagocytosis capabilities of these white blood cells, enhancing the attack of these cells against cancer cells, cells of infectious microorganisms, and cells infected with pathogens.

In one aspect, the invention includes bispecific binding molecules, comprising a first binding determinant which binds an Fcα receptor and a second binding determinant which binds one or more target antigens. Preferably, the first determinant binds a site on the FcαR that is different from the binding site for endogenous IgA. In a preferred embodiment, the target antigen bound by the second binding determinant of the bispecific molecules of the invention is a cancer cell antigen. In a more preferred embodiment the cancer cell antigen is an antigen of a cancer of the breast, ovary, testis, lung, colon, rectum, pancreas, liver, central nervous system, head and neck, kidney, bone, blood or lymphatic system. In another preferred embodiment, the target antigen is an infectious disease antigen from a pathogen or pathogen-infected cell. In yet another embodiment, the invention features treatment of an autoimmune disease with a composition that binds a receptor for IgA, causing modulation of the receptor such that further binding of IgA to that receptor is decreased.

A preferred embodiment of bispecific molecules of the subject invention comprise molecules with binding determinants for a receptor of the human EGF-like receptor family and mucine antigens, which are overexpressed by certain tumor cells.

The bispecific molecules of the invention emcompass molecules that are comprised in part of binding determinants of antibodies, and the molecules of the invention include those that are engineered to include at least one antibody or an antibody fragment. The bispecific binding molecules of the invention preferably comprise a binding determinant from an IgG antibody or IgG fragment, including an Fab, Fab', F(ab')$_2$, Fv, and single chain Fv. A preferred bispecific binding molecule of the invention comprises a first binding determinant that is at least a functional fragment of antibody A77 and a second binding determinant that binds a cancer cell antigen, a pathogen antigen, or an antigen on an infected cell. The invention includes nucleic acid sequences of the $V_H$ and $V_K$ regions of the A77 antibody and the predicted amino acid sequences of these regions, and these sequence are preferably used for humanizing the A77 binding determinants for therapeutic multispecific molecules. Preferably the second binding determinant of the molecules of the invention is at least a functional fragment of antibody 520C9, antibody H425 or antibody CC49. A preferred embodiment carries one binding determinant for FcαR and one for the HER/neu antigen found for example on tumors of the breast, ovary, and lung.

Several methods of producing bispecific binding molecules are encompassed by the invention, including by chemical linkage of the binding determinants, and by recombinant genetic methods. Recombinant bispecific molecules encoded by nucleic acid sequences carrying genes encoding binding determinants which are thus genetically linked are encompassed by the invention. Further, bispecific binding molecules of the invention are produced by cell fusion of two antibody-producing cell lines carrying the respective nucleic acid sequences encoding the binding determinants, such as hybridoma cell lines, to obtain a progeny cell line producing the bispecific molecule of the invention.

In addition to bispecific binding molecules, the instant invention encompasses multispecific binding molecules which comprise at least a first binding determinant which binds an Fcα receptor and a second binding determinant which binds a target antigen, and at least a third binding determinant. Binding of the first determinant of these multi specific binding molecules to FcαR is not inhibited by human immunoglobulin A, so there is no competition for binding by endogenous IgA molecules. Multispecific binding molecules encompass bispecific and trispecific compositions, and those with four or more binding determinants. A preferred embodiment of a trispecific binding molecule carries an additional binding determinant that binds to an Fc receptor that is not an Fcα receptor, including for example a binding determinant for CD2, CD3, Fcγ receptor, Fcε receptor, Fcδ receptor and/or Fcμ receptor, these determinants being in addition to the first binding determinant to Fcα receptor. The most preferred embodiment of an additional binding determinant for an FcR is a determinant for Fcγ receptor. For a multispecific binding molecule of the invention carrying a binding determinant for an Fcγ receptor, binding to FcγR is not inhibited by human IgG, since the molecule binds Fcγ at a different epitopic site from IgG binding of FcγR. By incorporating at least binding determinant for each of FcαR and FcγR into a single molecule, the therapeutic capability of the molecule is increased to enhance affinity and kinetics of binding of white blood cells to tumor cells or cells of pathogenic organisms or pathogen-infected cells, increasing opportunities for cytolysis and phagocytosis of these targets.

The preferred embodiment of the invented multispecific binding molecules with a determinant for Fcα, is a molecule that carries a third binding determinant that binds to a second target antigen or a second target epitope on a cancer cell, a pathogen, or a pathogen-infected cell. The preferred means of producing these molecules is by chemical linkage of the binding determinants, however the invention encompasses also multispecific binding molecules which are recombinantly produced, or which are produced by cell fusion of two or more cell lines each of which carries the nucleic acid sequences encoding the binding determinants. Preferably at least one binding determinant is an antibody or an antibody fragment, and to improve the success of the outcome during continued treatment of humans, the binding determinant is a humanized antibody, which is engineered to minimize the number of foreign epitopes born by the molecule.

A preferred embodiment of the multispecific binding molecules of this invention is comprised of one or more binding determinants for target cancer cell antigens, particularly cancer cell antigens from breast, ovary, testis, lung, colon, rectum, pancreas, liver, central nervous system, head and neck, kidney, bone, blood and lymphatic system cancers. A different preferred embodiment of the invented multispecific binding molecules comprises, as the target antigen, infectious disease antigens from pathogens or pathogen-infected cells. Infectious disease antigens and those expressed on infected cells include those from infections by bacteria, fungi, protozoa, and viruses. Suitable targets among cancer cell antigens are preferably members of the human EGF-like receptor family, more preferably the cancer cell antigen is an EGF receptor, and most preferably the cancer cell antigen is HER-2/neu, HER-3, HER-4, or a heteromultimeric receptor comprised of at least one HER subunit. Additional preferred cancer cell antigens include carcinoembryonic antigen, gastrin releasing peptide receptor antigen, and TAG 72.

A most preferred multispecific binding molecule comprises at least a first binding determinant that is at least a functional fragment of antibody A77 and a second binding determinant that binds an antigen of a cancer cell, a cell of a pathogenic organism, or a pathogen-infected cell. In preferred embodiments of A77-derived multispecific binding molecules with a cancer antigen binding determinant, the preferred second binding determinant is at least a functional fragment of antibody 520C9 or antibody CC49. The first binding determinant for an Fcα receptor preferably binds a receptor on a white blood cell. The types of white blood cells to which the molecules bind are preferably macrophages, monocytes, neutrophils, eosinophils, and lymphocytes.

Yet another aspect of the invention comprises multispecific binding molecules in which the molecule includes at least one antigen from a pathogen or pathogen-infected cell, or an antigen from a cancer cell. The molecules of this particular embodiment can serve to deliver these antigens as a vaccine directly to the antigen presenting cells of the immune system to immunize the recipient against an infectious disease or a cancer. These antigens can be taken from known antigenic protein sequences of bacteria, viruses, fungi and protozoans, and from cells infected with these pathogen, or from cancer cells, to immunize the recipient.

The multispecific binding molecules of the invention comprise binding determinants from antibody or antibody fragment molecules which preferably are IgG or IgG fragments. Antibody fragments are preferably Fab, Fab', F(ab')$_2$, Fv, or single chain Fv as sources of binding determinants for construction of the multispecific binding molecules.

Another feature of multi specific binding molecules in which the first binding determinant binds FcαR and the second binding determinant binds an antigen of a target cell, encompasses a third binding determinant which binds to a different antigen on the same target cell as the second binding determinant. Further, embodiments encompass a third binding determinant which binds to a different epitope on the same target antigen as the second binding determinant. These determinants provide a two-fold binding capacity of the multi specific molecule to the target to link it to an immune effector cell, for cytolysis and phagocytosis.

The invention also provides a method for eliminating an unwanted cell in a subject, comprising administering to the subject a therapeutically effective dose of a multispecific binding molecule, which comprises at least a first binding determinant which binds an Fcα receptor and a second binding determinant which binds an antigen on the unwanted cell, in a pharmaceutically acceptable carrier. An even more preferred embodiment of the method for eliminating unwanted cells in a subject involves treating the subject in addition with an agent that enhances the number or activity of Fcα receptors, for example, treating the subject with a cytokine. Preferred cytokines for administration during treatment with the invented composition treatment include at least one of G-CSF, GM-CSF, IFN-γ, and TNF, and protocols involving treatment with the molecules of the subject invention and more than one additional therapeutic agent are envisioned. Another preferred embodiment of the invention is a method for eliminating an unwanted cell in a subject, comprising obtaining an aliquot of a sample of blood or blood cells from said subject, treating said blood or blood cells ex vivo with a therapeutically effective dose of a multispecific binding molecule of the invention in a pharmaceutically acceptable carrier, said binding molecule comprising a first binding determinant which binds an Fcα receptor and a second binding determinant which binds one or more target antigens, and returning said treated blood or blood cells to the subject. Preferably, the cells of the sample of blood are isolated and expanded in culture, and more preferably, the cells of said sample of blood are treated with agents that enhance the number or activity of Fcα receptors.

In a aspect, the invention provides a method for treatment of a subject with an infectious disease, comprising administration to the patient of a therapeutically effective dose in a pharmaceutically acceptable carrier of a multispecific binding molecule, wherein a first binding determinant binds an Fcα receptor and a second binding determinant binds a target antigen from a pathogen or a pathogen-infected cell, enhancing the capacity of the immune system to eliminate the infection.

In yet another embodiment, the invention provides a method for immunizing a subject against a cancer antigen or an antigen found on a pathogen or a cell infected by a, comprising administration in a pharmaceutically acceptable carrier of a composition of a multi specific binding agent bearing one or more antigens of a pathogenic infectious organism, or of an antigen of infected cells, or of a cancer cell.

BRIEF DESCRIPTION OF THE DRAWINGS

FIG. 14 shows the DNA sequence of the light chain variable $V_K$ region of the gene encoding the A77 anti-FcαR antibody (SEQ ID NO: 5), and the predicted amino acid residue sequence (SEQ ID NO: 6).

FIG. 15 shows the DNA sequence of the heavy chain variable $V_H$ region of the gene encoding the A77 anti-FcαR antibody (SEQ ID NO: 7), and the predicted amino acid residue sequence (SEQ ID NO: 8).

DETAILED DESCRIPTION OF THE INVENTION

1. Definitions

Figure 1:
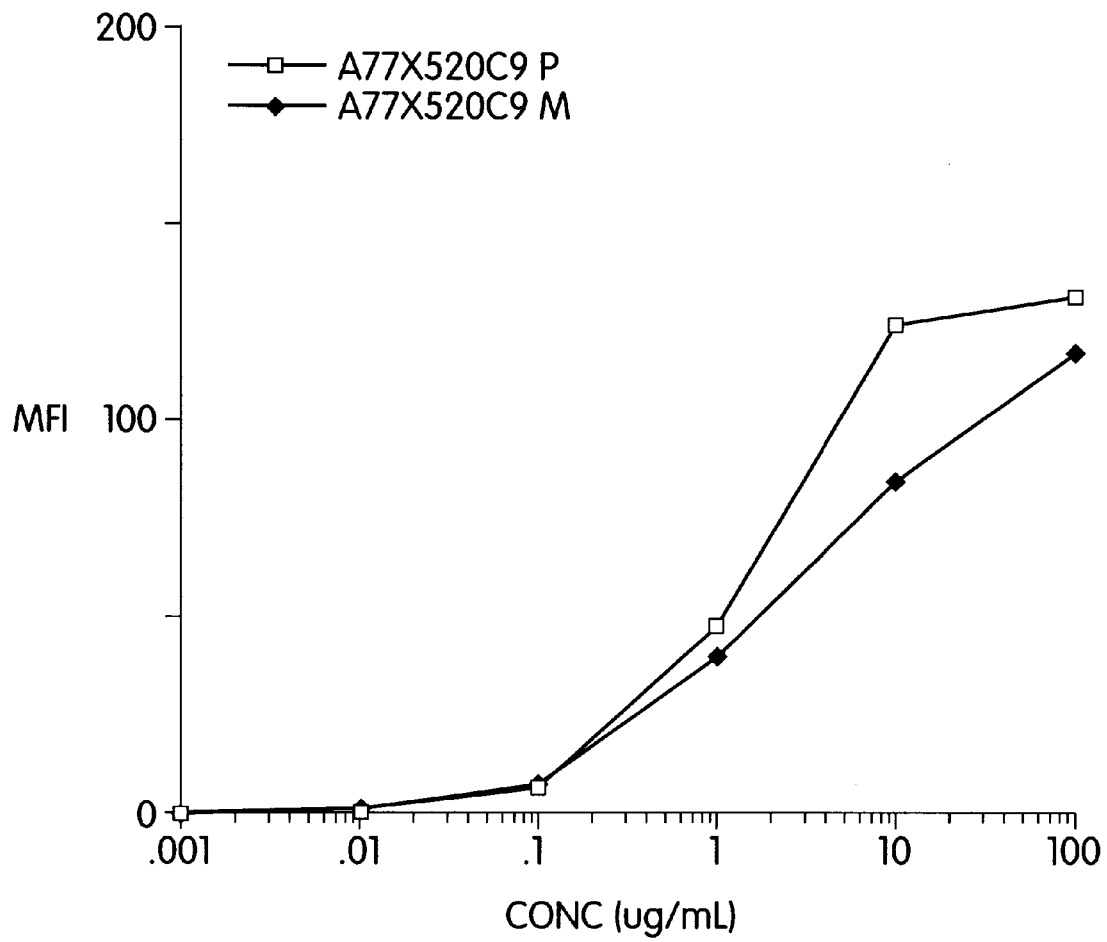
FIG. 1 is a graph showing the extent of binding of A77×520C9, the anti-FcαR×anti-HER2/neu BsAb, as a function of concentration in micrograms per milliliter, to neutrophils (PMN, open squares) and to monocytes (solid squares), in which mean fluorescence intensity analyzed by FACScan is the measure of binding.

Definitions of the terms and phrases as used herein should have the meanings indicated below. An antibody (or fragment thereof) is used in the invention as a component of multispecific agents which cause association of a cytolytic, phagocytic white blood cell with a tumor cell, or unwanted infectious disease agent or infected cell. Antibodies suitable for use in the methods of the invention are available in the art (e.g., from the American Type Culture Collection, 10801 University Blvd., Manassas Va. 20110-2209 or commercially, e.g., from Becton-Dickinson or Immunotech) or can be prepared by standard techniques for making antibodies. The term "antibody" as used herein refers to immunoglobulin molecules and immunologically active determinants of immunoglobulin molecules, i.e., molecules that contain an antigen binding site which specifically binds (immunoreacts with) an antigen. Structurally, the simplest naturally occurring antibody (e.g., IgG) comprises four polypeptide chains, two copies of a heavy (H) chain and two of a light (L) chain, all covalently linked by disulfide bonds. Specificity of binding in the large and diverse set of antibodies is found in the variable (V) determinant of the H and L chains; regions of the molecules that are primarily structural are constant (C) in this set.

The binding sites of the proteins that comprise an antibody, i.e., the antigen-binding functions of the antibody, are localized by analysis of fragments of a naturally-occurring antibody. Thus, antigen-binding fragments are also intended to be designated by the term "antibody." Examples of binding fragments encompassed within the term antibody include: a Fab fragment consisting of the $V_L$, $V_H$, $C_L$ and $C_{H1}$ domains; an Fd fragment consisting of the $V_H$ and $C_{H1}$ domains; an Fv fragment consisting of the $V_L$ and $V_H$ domains of a single arm of an antibody; a dAb fragment (Ward et al., 1989 Nature 341: 544–546) consisting of a $V_H$ domain; an isolated complementarity determining region (CDR); and an F(ab')$_2$ fragment, a bivalent fragment comprising two Fab' fragments linked by a disulfide bridge at the hinge region. These antibody fragments are obtained using conventional techniques well-known to those with skill in the art, and the fragments are screened for utility in the same manner as are intact antibodies. The term "antibody" is further intended to include bispecific and chimeric molecules having at least one antigen binding determinant derived from an antibody molecule. Furthermore, although the H and L chains of an Fv fragment are encoded by separate genes, a synthetic linker can be made that enables them to be made as a single protein chain (known as single chain antibody, sAb; Bird et al. 1988 *Science* 242: 423–426; and Huston et al. 1988 *PNAS* 85: 5879–5883) by recombinant methods. Such single chain antibodies are also encompassed within the term "antibody", and may be utilized as binding determinants in the design and engineering of a multispecific binding molecule. Antibody fragments are also useful for modulating the number of receptors for that antibody on the surface of cells, and for obtaining agents that mimic this activity, by screening for such agents in an assay for modulation of the receptor.

Polyclonal antibodies are produced by immunizing animals, usually a mammal, by multiple subcutaneous or intraperitoneal injections of an immunogen (antigen) and an adjuvant as appropriate. As an illustrative embodiment, animals are typically immunized against a protein, peptide or derivative by combining about 1 μg to 1 mg of protein capable of eliciting an immune response, along with an enhancing carrier preparation, such as Freund's complete adjuvant, or an aggregating agent such as alum, and injecting the composition intradermally at multiple sites. Animals are later boosted with at least one subsequent administration of a lower amount, as ⅕ to ¹⁄₁₀ the original amount of immunogen in Freund's complete adjuvant (or other suitable adjuvant) by subcutaneous injection at multiple sites. Animals are subsequently bled, serum assayed to determine the specific antibody titer, and the animals are again boosted and assayed until the titer of antibody no longer increases (i.e., plateaus).

Such populations of antibody molecules are referred to as "polyclonal" because the population comprises a large set of antibodies each of which is specific for one of the many differing epitopes found in the immunogen, and each of which is characterized by a specific affinity for that epitope. An epitope is the smallest determinant of antigenicity, which for a protein, comprises a peptide of six to eight residues in length (Berzofsky, J. and I. Berkower, (1993) in Paul, W., Ed., *Fundamental Immunology*, Raven Press, N.Y., p.246). Affinities range from low, e.g. $10^{-6}$M, to high, e.g., $10^{-11}$M. The polyclonal antibody fraction collected from mammalian serum is isolated by well known techniques, e.g. by chromatography with an affinity matrix that selectively binds immunoglobulin molecules such as protein A, to obtain the IgG fraction. To enhance the purity and specificity of the antibody, the specific antibodies may be further purified by immunoaffinity chromatography using solid phase-affixed immunogen. The antibody is contacted with the solid phase-affixed immunogen for a period of time sufficient for the immunogen to immunoreact with the antibody molecules to form a solid phase-affixed immunocomplex. Bound antibodies are eluted from the solid phase by standard techniques, such as by use of buffers of decreasing pH or increasing ionic strength, the eluted fractions are assayed, and those containing the specific antibodies are combined.

The term "monoclonal antibody" or "monoclonal antibody composition" as used herein refers to a preparation of antibody molecules of single molecular composition. A monoclonal antibody composition displays a single binding specificity and affinity for a particular epitope. Monoclonal antibodies can be prepared using a technique which provides for the production of antibody molecules by continuous growth of cells in culture. These include but are not limited to the hybridoma technique originally described by Kohler and Milstein (1975, *Nature* 256: 495–497; see also Brown et al. 1981 *J. Immunol* 127: 539–46; Brown et al., 1980, *J Biol Chem* 255: 4980–83; Yeh et al., 1976, *PNAS* 76: 2927–31; and Yeh et al., 1982, *Int. J Cancer* 29: 269–75) and the more recent human B cell hybridoma technique (Kozbor et al., 1983, *Immunol Today* 4: 72), EBV-hybridoma technique (Cole et al., 1985, Monoclonal Antibodies and Cancer Therapy, Alan R. Liss, Inc., pp. 77–96), and trioma techniques.

A monoclonal antibody can be produced by the following steps. In all procedures, an animal is immunized with an antigen such as a protein (or peptide thereof) as described above for preparation of a polyclonal antibody. The immunization is typically accomplished by administering the immunogen to an immunologically competent mammal in an immunologically effective amount, i.e., an amount sufficient to produce an immune response. Preferably, the mammal is a rodent such as a rabbit, rat or mouse. The mammal is then maintained on a booster schedule for a time period sufficient for the mammal to generate high affinity antibody molecules as described. A suspension of antibody-producing cells is removed from each immunized mammal secreting the desired antibody. After a sufficient time to generate high affinity antibodies, the animal (e.g., mouse) is sacrificed and antibody-producing lymphocytes are obtained from one or more of the lymph nodes, spleens and peripheral blood. Spleen cells are preferred, and can be mechanically separated into individual cells in a physiological medium using methods well known to one of skill in the art. The antibody-producing cells are immortalized by fusion to cells of a mouse myeloma line. Mouse lymphocytes give a high percentage of stable fusions with mouse homologous myelomas, however rat, rabbit and frog somatic cells can also be used. Spleen cells of the desired anti-bodyproducing animals are immortalized by fusing with myeloma cells, generally in the presence of a fusing agent such as polyethylene glycol. Any of a number of myeloma cell lines suitable as a fusion partner are used with to standard techniques, for example, the P3-NS1/1-Ag4-1, P3-x63-Ag8.653 or Sp2/O-Ag14 myeloma lines, available from the American Type Culture Collection (ATCC), Rockville, Md.

The fusion-product cells, which include the desired hybridomas, are cultured in selective medium such as HAT medium, designed to eliminate unfused parental myeloma or lymphocyte or spleen cells. Hybridoma cells are selected and are grown under limiting dilution conditions to obtain isolated clones. The supernatants of each clonal hybridoma is screened for production of antibody of desired specificity and affinity, e.g., by immunoassay techniques to determine the desired antigen such as that used for immunization. Monoclonal antibody is isolated from cultures of producing cells by conventional methods, such as ammonium sulfate precipitation, ion exchange chromatography, and affinity chromatography (Zola et al., Monoclonal Hybridoma Antibodies: Techniques And Applications, Hurell (ed.), pp. 51–52, CRC Press, 1982). Hybridomas produced according to these methods can be propagated in culture in vitro or in vivo (in ascites fluid) using techniques well known to those with skill in the art.

For therapeutic use of antibodies of non-human origin in humans, the non-human "foreign" epitopes elicit immune response in the patient. If sufficiently developed, a potentially lethal disease known as HAMA (human antibodies against mouse antibody) may result. To eliminate or minimize HAMA, it is desirable to engineer chimeric antibody derivatives, i.e., "humanized" antibody molecules that combine the non-human Fab variable region binding determinants with a human constant region (Fc). Such antibodies are characterized by equivalent antigen specificity and affinity of monoclonal and polyclonal antibodies described above, and are less immunogenic when administered to humans, and therefore more likely to be tolerated by the patient.

Chimeric mouse-human monoclonal antibodies (i.e., chimeric antibodies) can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted. (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125, 023; Better et al. (1988 *Science* 240: 1041–1043); Liu et al. (1987) *PNAS* 84: 3439–3443; Liu et al., 1987, *J. Immunol.* 139: 3521–3526; Sun et al. (1987) *PNAS* 84: 214–218; Nishimura et al., 1987, *Canc. Res.* 47: 999–1005; Wood et al. (1985) *Nature* 314: 446–449; and Shaw et al., 1988, *J. Natl Cancer Inst.* 80: 1553–1559.)

The chimeric antibody can be further humanized by replacing sequences of the Fv variable region which are not directly involved in antigen binding with equivalent sequences from human Fv variable regions. General reviews of humanized chimeric antibodies are provided by Morrison, S. L., 1985, *Science* 229: 1202–1207 and by Oi et al., 1986, *BioTechniques* 4: 214. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from 7E3, an anti-GPII$_b$III$_a$ antibody producing hybridoma. The recombinant DNA encoding the chimeric antibody, or fragment thereof, can then be cloned into an appropriate expression vector. Suitable humanized antibodies can alternatively be produced by CDR substitution U.S. Pat. No. 5,225,539; Jones et al. 1986 *Nature* 321: 552–525; Verhoeyan et al. 1988 *Science* 239: 1534; and Beidler et al. 1988 *J. Immunol.* 141: 4053–4060).

Human mAb antibodies directed against human proteins can be generated using transgenic mice carrying the complete human immune system rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 *Nature* 368: 856–859; Green, L. L. et al. 1994 *Nature Genet.* 7: 13–21; Morrison, S. L. et al. 1994 *Proc. Natl. Acad. Sci. USA* 81: 6851–6855; Bruggeman et al. 1993 *Year Immunol* 7: 33–40; Tuaillon et al. 1993 *PNAS* 90: 3720–3724; Bruggeman et al. 1991 *Eur J Immunol* 21: 1323–1326).

Monoclonal antibodies can also be generated by other methods well known to those skilled in the art of recombinant DNA technology. An alternative method, referred to as the "combinatorial antibody display" method, has been developed to identify and isolate antibody fragments having a particular antigen specificity, and can be utilized to produce monoclonal antibodies (for descriptions of combinatorial antibody display see e.g., Sastry et al. 1989 *PNAS* 86: 5728; Huse et al. 1989 *Science* 246: 1275; and Orlandi et al. 1989 *PNAS* 86: 3833). After immunizing an animal with an immunogen as described above, the antibody repertoire of the resulting B-cell pool is cloned. Methods are generally known for obtaining the DNA sequence of the variable regions of a diverse populby using a mixture ofin molecules by using a mixture of oligomer primers and PCR. For instance, mixed oligonucleotide primers corresponding to the 5' leader (signal peptide) sequences and/or framework 1 (FR1) sequences, as well as primer to a conserved 3' constant region primer can be used for PCR amplification of the heavy and light chain variable regions from a number of murine antibodies (Larrick et al., 1991, *Biotechniques* 11: 152–156). A similar strategy can also been used to amplify human heavy and light chain variable regions from human antibodies (Larrick et al., 1991, *Methods: Companion to Methods in Enzymology* 2: 106–110).

Immune response to "foreign" antigens comprises the notion that "self" proteins and other molecules expressed within an organisms are not antigenic or immunogenic to that organism. In fact, discrimination between isologous or homologous determinants and foreign, or heterologous determinants is achieved through maturation of the immune system of an organism during development of the immune system. A system of selection against immune cells bearing antibodies with binding determinants to "self" occurs, so that when mature the immune system does not attack proteins or other molecules native to the organism. In certain pathological conditions known as "autoimmune diseases," however, such discrimination is not as accurate, and endogenous structures may be subject to attack from the immune system. Examples of autoimmune diseases and conditions in which there is autoimmune exacerbation of symptoms include systemic lupus erythematosus, myasthemia gravis, multiple sclerosis, and rheumatoid arthritis. Compositions of the instant invention which are capable of binding to a site on the Fcα receptor, by virtue of comprising a binding determinant of an antibody for a site on this receptor, can also modulate the number of these receptors on the cell surface, and accordingly are potential agents for treatment of autoimmune diseases. Further, amino acid residue sequence data of the Fv regions of the antibody binding determinant is the basis for obtaining a three-dimensional model of the protein features, such as size, charge, and shape of the set of residues which comprise this binding site, so that agents which mimic this binding site may be designed.

The agents of the invention are administered to subjects in biologically compatible forms suitable for pharmaceutical administration in vivo to produce a therapeutic response against a cancer or an infectious disease. By "biologically compatible form suitable for administration in vivo" is meant a form of the protein to be administered in which any toxic effects and side effects are outweighed by the therapeutic effects of the composition.

The term "subject," as used herein, refers to a living animal or human in need of susceptible to a condition, in particular a "cancer or infectious disease" as defined below. The subject is an organism possessing leukocytes capable of responding to antigenic stimulation and growth factor stimulation. In preferred embodiments, the subject is a mammal, including humans and non-human mammals such as dogs, cats, pigs, cows, sheep, goats, horses, rats, and mice. In the most preferred embodiment, the subject is a human. The term "subject" does not preclude individuals that are entirely normal with respect to cancer, infectious disease, or normal in all respects.

The term "patient," as used herein, refers to a human subject who has presented at a clinical setting with a particular symptom or symptoms suggesting one or more therapeutic regimens. A patient may be in need of further categorization by clinical procedures well-known to medical practitioners of the art (or may have no further disease indications and appear to be in any or all respects normal). A patient's diagnosis may alter during the course of disease progression, such as development of further disease symptoms, or remission of the disease, either spontaneously or during the course of a therapeutic regimen or treatment, or rediagnosis as being entirely of normal condition.

The term "infectious disease" is meant to include disorders caused by one or more species of bacteria, viruses, fungi, and protozoans, which are diseaseproducing organisms collectively referred to as "pathogens." In this invention, pathogens are exemplified, but not limited to, *Mycobacterium tuberculosis, M. leprae, Pseudomonas aeruginosa, Shigella dysenteria, Salmonella typhi, S. paratyphi, Staphylococcus aureus, Streptococcus hemolyticus, Hemophilus pneumoniae, Escherichia coli* serotype 0157, Chlamydia species, Helicobacter species; HIV-1,-2, and -3, HSV-I and -II, non-A non-B non-C hepatitis virus, pox viruses, rabies viruses; Aspergillus species; *Entamoeba histolytica*, Giardia species; and Newcastle disease virus. Obtaining unique epitopes from these organisms by screening proteins and by assaying peptides in vitro are commonly known to those skilled in the art.

II. Multispecific molecules

The instant invention relates in one embodiment to recombinant multispecific molecules, which have affinity for and are capable of binding at least two different entities. Multispecific molecules can include bispecific molecules comprised of a binding determinant for an Fc receptor and a binding determinant for a target. The preferred multispecific molecules for the instant invention include molecules which are comprised of at least one copy of a binding determinant which binds specifically to an Fcα receptor or target; or molecules comprised of at least one binding determinant which binds an Fcα receptor, one binding determinant for a target and additionally one or more binding determinants that recognize other molecules. A preferred multispecific molecule is a bispecific antibody (BsAb), which carries at least two different binding determinants, at least one of which is of antibody origin.

A "binding determinant for an Fcα receptor" refers to an antibody, a functional antibody fragment (e.g., Fab fragment) or a ligand such as an engineered binding protein that recognizes and binds an Fcα receptor on an effector cell. Preferred antibodies for use in the subject invention bind the Fcα receptor on an effector cell (white blood cell) at a site which is not bound by endogenous immunoglobulin A (IgA). Most preferably, the anti-Fcα receptor $V_H$ and $V_L$ portion binds a human FcαR. Preferred humanized anti-FcαR monoclonal antibodies are described, the teachings of which are fully incorporated herein by reference. The antibody that comprises the BsAb or multi specific molecule of the invention may be whole, i.e. having heavy and light chains or any fragment thereof, e.g., Fab or (Fab')$_2$ fragment. The antibody further may be a light chain or heavy chain dimer, or any minimal fragment thereof such as a Fv or a single chain construct as described in Ladner et al. (U.S. Pat. No. 4,946,778, issued Aug. 7, 1990), the contents of which is expressly incorporated by reference.

An "effector cell" as used herein refers to an immune cell which is a leukocyte or a lymphocyte. Specific effector cells express specific Fc receptors and carry out specific immune functions. For example, monocytes, macrophages, neutrophils, eosinophils, and lymphocytes which express FcαR are involved in specific killing of target cells and presenting antigens to other components of the immune system, or binding to cells that present antigens. The expression of a particular FcR on an effector cell can be regulated by humoral factors such as cytokines. For example, expression of FcγRI has been found to be up-regulated by interferon gamma (IFN-γ). This enhanced expression increases the cytotoxic activity of FcγRI-bearing cells against targets.

The recombinant antibodies or antibody fragments which specifically bind to an Fc receptor, are preferably "humanized" i.e. carry portions derived from a human antibody, but having at least a portion of a complementarity determining region (CDR) derived from a non-human antibody. Ordinarily that portion which is "humanized" is selected to provide specificity of the humanized antibody to bind a human Fc receptor. The humanized antibody has CDR portions derived from a non-human antibody and the "constant" portions of the antibody molecule are of human origin.

The portion of the non-human CDR inserted into the human antibody is selected to be sufficient for allowing binding of the humanized antibody to the Fcα receptor. A sufficient portion may be selected by inserting a portion of the CDR into the human antibody and testing the binding capacity of the created humanized antibody using flow cytometry or enzyme linked immunosorbent assay (ELISA). All of the CDRs of a particular human antibody may be replaced with at least a portion of a non-human CDR or only some of the CDRs may be replaced with non-human CDRs. It is only necessary to replace the number of CDRs required for binding of the humanized antibody to the Fc receptor.

An antibody can be humanized by any method, which is capable of replacing at least a portion of a CDR of a human antibody with a CDR derived from a non-human antibody. Winter describes a method which may be used to prepare the humanized antibodies of the present invention (UK Patent Application GB 2188638A, filed on Mar. 26, 1987), the contents of which is expressly incorporated by reference. The human CDRs may be replaced with non-human CDRs using oligonucleotide site-directed mutagenesis as described in International Application WO 94/10332 entitled, Humanized Antibodies to Fc Receptors for Immunoglobulin G on Human Mononuclear Phagocytes.

In addition to an anti-Fcα receptor portion, the claimed multispecific molecules can comprise a binding determinant for a target i.e. an antibody, a functional antibody fragment or a ligand that recognizes and binds a pathogen (e.g., viruses, bacteria, fungi, protozoa), a pathogen infected cell, a cancer or tumor cell (e.g., breast, ovarian, prostate, testicular, lung, colon, rectum, pancreas, liver, central nervous system, head and neck, kidney, bone, blood, and lymphatic system) or other unwanted cell in a subject (e.g., a human or animal) or an antigen or modified form thereof. Additionally, the target portion may comprise or be directed against an antigen. A preferred embodiment contains an antigen that can be used to induce a specific immune response against a chronic infection, against a tumor or cancer cell, or to deplete antigen in the circulation. A different particularly preferred embodiment has an antigen that is attached to a multivalent molecule containing a binding determinant for an FcR, which stimulates the immune system by directing the antigen to an antigen presenting cell.

In one embodiment of the invention, the multispecific molecule contains a binding determinant or ligand which interacts with a molecule. In a preferred embodiment, the binding determinant binds a protein, e.g., a protein on a target cell, such as a cancer cell, or a cell of an infectious disease agent or the agent itself or an infected cell. Preferred binding determinants include antibodies, fragments of antibodies, and receptors for growth factors or differentiation factors. For example, a multivalent molecule can comprise an epidermal growth factor (EGF), or at least a portion or modified form that is capable of interacting with a receptor, e.g., an epidermal growth factor receptor EGF-R, or an antibody to EGF-R. A particularly preferred embodiment of the invention comprises a BsAb carrying a binding determinant for an human EGF-like receptor, including the EGF-R, HER2/neu, HER3, HER4, etc. In yet another preferred embodiment, the binding determinant is for the tumor antigen TAG 72 found e.g. on tumors of the breast, colon, and ovary.

In another preferred embodiment of the invention, the ligand is a small peptide, such as bombesin, gastrin-releasing peptide (GRP), litorin, neuromedin B, or neuromedin C. The sequences of the peptides can be found, e.g., in U.S. Pat. No. 5,217,955, the content of which is incorporated herein by reference. The ligand can also be a modified form of any of these peptides. The modification can increase binding to the receptor, decrease binding, or not affect the binding to a receptor. The modification of the ligand can also transform an agonist into an antagonist, such that the ligand inhibits rather than stimulates cell proliferation. Modification of the ligand can be an addition, a deletion, a substitution, or a modification of at least one amino acid.

In another preferred embodiment of the invention, a multispecific or bispecific molecule comprises an antigen. As used herein, the term "antigen" means any natural or synthetic immunogenic substance, a fragment or portion of an immunogenic substance, a peptidic epitope, or a hapten. In one embodiment of the invention, a bi- or multispecific molecule is employed to target an antigen, e.g., tetanus toxoid to the cell to enhance the processes of internalization and presentation by these cells, and ultimately, to stimulate an immune response therein. In a specific embodiment, the bispecific binding agent specifically binds the antigen (either directly, to an epitope of the antigen, or indirectly, to an epitope attached to the antigen) and, at the same time, binds a surface receptor of an antigen-presenting cell which can internalize antigen for processing and presentation. In another embodiment, the antigen is linked to the multi- or bispecific molecule and at the same time binds a surface receptor of an antigen-presenting cell. In a preferred embodiment the antigen is covalently attached to the multispecific molecule by genetic or chemical means The receptor-binding component of the bi- or multispecific molecule (and thus the bi- or multispecific molecule, itself) binds the receptor of the antigen-presenting cell at a site different and distinct from the naturally-occupying ligand. Thus, binding of the multi specific molecule occurs without competition by the natural ligand for the receptor. As a result, binding to the receptor will not be prevented by physiological levels of the ligand and the targeted receptor will remain capable of binding the molecule of the invention and the ligand.

One type of antigen can be an allergen. An "allergen" refers to a substance that can induce an allergic or asthmatic response in a susceptible subject. The number of allergens that elicit a sensitive response in a proportion of a population is enormous, and includes pollens, insect venoms, animal dander, dust mite proteins, fungal spores and drugs (e.g. penicillin). Examples of natural animal and plant allergens include proteins specific to the following genera: Felis (*Felis domesticus*); Canis (*Canis familiaris*); Dermatophagoides (e.g. *Dermatophagoides farinae*); Periplaneta (e.g. *Periplaneta americana*); Ambrosia (*Ambrosia artemiisfolia*; Lolium (e.g. *Lolium perenne* or *Lolium multiflorum*); Cryptomeria (*Cryptomeria japonica*); Alternaria (*Alternaria alternata*); Alder; Alnus (*Alnus gultinosa*); Betula (*Betula verrucosa*); Quercus (*Quercus alba*); Olea (*Olea europa*); Artemisia (*Artemisia vulgaris*); Plantago (e.g. *Plantago lanceolata*); Parietaria (e.g. *Parietaria officinalis* or *Parietaria judaica*); Blattella (e.g. *Blattella germanica*); Apis (e.g. *Apis multiflorum*); Cupressus (e.g. *Cupressus sempervirens, Cupressus arizonica* and *Cupressus macrocarpa*); Juniperus (e.g. *Juniperus sabinoides, Juniperus virginiana, Juniperus communis* and *Juniperus ashei*) Thuya (e.g. *Thuya orientalis*); Chamaecyparis (e.g. *Chamaecyparis obtusa*); Agropyron (e.g. *Agropyron repens*); Secale (e.g. *Secale cereale*); Triticum (e.g. *Triticum aestivum*); Dactylis (e.g. *Dactylis glomerata*); Festuca (e.g. *Festuca elatior*); Poa (e.g. *Poapratensis* or *Poa compressa*); Avena (e.g. *Avena sativa*); Holcus (e.g. *Holcus lanatus*); Anthoxanthum (e.g. *Anthoxanthum odoratum*); Arrhenatherum (e.g. *Arrhenatherum elatius*); Agrostis (e.g. *Agrostis alba*); Phleum (e.g. *Phleum partense*); Phararis (e.g. *Phalaris arundinacea*); Paspalum (e.g. *Paspalum notatum*); Sorghum (e.g. *Sorghum halepensis*); and Bromus (e.g. *Bromus inermis*).

Many allergens are found in airborne pollens of ragweed, grasses, or trees, or in fungi, animals, house dust, or foods. As a class, they are relatively resistant to proteolytic digestion. Preferable allergens are those which bind to IgE on mast cells and basophils, thereby causing a range of symptoms from inflammation and asthma to a type I anaphylaxis hypersensitivity reaction.

In another preferred embodiment, a binding determinant is specific for an antigen on an infectious disease agent or an infected cell, as defined supra. In some cases, it may be desirable to couple a substance which is weakly antigenic or nonantigenic in its own right (such as a hapten) to a carrier molecule, such as a large immunogenic protein (e.g., a bacterial toxin) for administration. In these instances, the bispecific binding reagent can be made to bind an epitope of the carrier to which the substance is coupled, rather than an epitope of the substance itself.

The antigen that can be linked either directly, or indirectly, to a multior bispecific molecule of the invention can be soluble or particulate; it may carry B cell epitopes, T cell epitopes or both. The antigen can be bacterial, fungal, viral or parasitic in origin. Often, the antigen will comprise a component of the surface structure of a pathogenic organism, or a surface structure in a cell infected by a pathogenic organism. For example, the antigen can comprise a viral surface structure such as an envelope glycoprotein of human immunodeficiency virus (HIV) or the surface antigen of hepatitis virus. In addition, the antigen can be associated with a diseased cell, such as a tumor cell, against which an immune response may be raised for treatment of the disease. The antigen can comprise a tumor-specific or tumorassociated antigen, such as the HER-2/neu proto-oncogene product which is expressed on human breast and ovarian cancer cells (Slamon et al. (1989) *Science* 244: 707). Another important cancer antigen which comprises a target of the BsAb of this invention is TAG 72, which has been identified on about 90% of colorectal cancers, 85% of breast tumors, and 95% of ovarian tumors (Johnson et al.(1986) *Cancer Res.* 46: 850–897; Bodmer, M. et al, European Patent Specification 0 348 442 B1; Mezes, P. et al. International Application WO 93/12231).

The cells of a subject can be exposed ex vivo or in vivo to the multispecific molecules of the invention, to target an antigen to antigen-presenting cells. Immune cells are separated and purified from subject blood, exposed to a multispecific molecule comprising the antigen, or the cells can be exposed to the antigen together with a multispecific molecule having a binding determinant for the antigen. After stimulation, cells are returned to the subject. Cells to be used in this procedure can also be treated with cytokines or other factors, for the purpose of, for example, up-regulating numbers of receptors per cell. Further, in vivo or ex vivo therapeutic use of the molecules can be enhanced by treatment of the subject with one or more cytokines or growth factors.

The method of this invention can be used to enhance or reinforce the immune response to an antigen. For example, the method is valuable for the treatment of chronic infections, such as hepatitis and AIDS, where the unaided immune system is unable to overcome the infection. It can also be used in the treatment of the acute stages of infection when reinforcement of immune response against the invading organism may be necessary.

The method can be used to reduce the dose of antigen required to obtain a protective or therapeutic immune response or in instances when the host does not respond or responds minimally to the antigen. Although generally desirable, the lowering of effective dose can be especially desirable when the antigen is toxic to the host such as is the case for allergies. Methods and uses for bi- or multispecific molecules comprising one or more antigens or comprising one or more binding determinants, e.g., an antibody interacting with an antigen, are further described in the published PCT application PCT/US91/07283.

III. Methods for Making Multispecific Molecules

The multispecific molecules described above can be made by a number of methods. For example, both specificities can be encoded in the same vector and expressed and assembled in the same host cell. This method is particularly useful where the multi-specific molecule is a mAb×mAb, mAb×Fab, Fab×F(ab')$_2$ or ligand×Fab fusion protein. A bispecific molecule of the invention can also be a single chain bispecific molecule, such as a single chain bispecific antibody, a single chain bispecific molecule comprising one single chain antibody and a binding determinant, or a single chain bispecific molecule comprising two binding determinants. Multispecific molecules can also be single chain molecules or may comprise at least two single chain molecules. Methods for preparing bi- or multivalent antibodies are described for example described in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013,653; U.S. Pat. No. 5,258,498; and U.S. Pat. No. 5,482,858.

Binding of the single chain molecules to their specific targets can be confirmed by bispecific ELISA, familiar to those skilled in the art. Alternatively, each specificity of a multispecific molecule can be generated separately and the resulting proteins or peptides chemically conjugated to one another. For example, two humanized antibodies or antibody fragments can be conjugated via sulfhydryl bonding of the C-terminus hinge regions of the two heavy chains as described in Examples, infra.

The bispecific molecules of the present invention can be prepared by conjugating the anti-FcR and anti-target portions using methods described in the following Examples or those well-known in the art. For example, a variety of coupling or cross-linking agents can be used for covalent conjugation. Examples of cross-linking agents include protein A, carbodiimide, N-succinimidyl-S-acetyl-thioacetate (SATA), N-succinimidyl-3-(2-pyridyldithio)propionate (SPDP), and sulfosuccinimidyl 4-(N-maleimidomethyl) cyclohexane-1-carboxylate (sulfo-SMCC) (see e.g., Karpovsky et al. (1984) J. Exp. Med. 160:1686; Liu, MA et al. (1985) Proc. Natl. Acad. Sci. USA 82:8648). Other methods include those described by Paulus (Behring Ins. Mitt. (1985) No. 78, 118–132); Brennan et al. (Science (1985) 229: 81–83), and Glennie et al. (J. Immunol. (1987) 139: 2367–2375). Examples of other cross-linking agents include ortho-phylenedimaleimide (o-PDM), protein A, carbodiimide. In the preferred embodiment for BsAb, the conjugating agent is oPDM. Other preferred conjugating agents are SATA and sulfo-SMCC, both available from Pierce Chemical Co. (Rockford, Ill.).

Based on their ability to bind FcR bearing immune cells and specific target cells, a particular embodiment of a multispecific molecule can be administered to a subject to treat or prevent reoccurrence of a variety of diseases or conditions, including: cancer (e.g., breast, ovarian, testicular, prostate, lung, brain, colon, rectum, pancreas, liver, central nervous system, head and neck, kidney, bone, blood and lymphatic system), pathogenic infections such as viral (such as HIV, HTLV and FELV), protozoan (such as *Toxoplasma gondii*), fungal (such as *Candida albicans*); and bacterial (such as *Staphylococcus aureus, Streptococcus hemolyticus* and *Mycobacterium tuberculosis*). Another aspect of the invention provides molecules that are useful for vaccination against diseases and cancer by including an antigen from disease organisms, from infected cells, from gene products of disease organisms or from cancer cells. For these purposes, the invention provides coare multispecich are multispecific molecules that link the useful operative antigen to a binding determinant that directs the antigen to the immune system. An Example provided herein describes a molecule which functions to target tetanus toxoid directly to FcαR on monocytes, resulting in stimulation of T cells at lower doses than is required by free tetanus toxoid.

For use in therapy, an effective amount of an appropriate multispecific molecule can be administered to a subject by any mode that allows the molecules to exert their intended therapeutic effect. Preferred routes of administration include oral, transdermal (e.g., via a patch), and injection (subcutaneous, intravenous, parenteral, intraperitoneal, intrathecal, etc.). The injection can be in a bolus or a continuous infusion. Further, the cells of a tissue, e.g. blood, may be removed from a patient, fractionated and cultured if appropriate to expand the cell number, treated ex vivo with the multispecific multivalent composition in a pharmaceutically acceptable carrier, and returned to the patent for therapy. During the ex vivo culture and expansion, a particular cell type may be selected, e.g. a monocyte population. Further, ex vivo cultured cells may be treated at various points during ex vivo culture and expansion, with agents to modify certain functional FcαR molecules. Agents include but are not limited to, growth factors, cytokines, lymphokines such as IFN-γ, G-CSF, TNF, and GM-CSF, and interleukins such as IL-2, IL-10 and IL-12.

A multispecific molecule is administered in conjunction with a pharmaceutically acceptable carrier. As used herein, the phrase "pharmaceutically acceptable carrier" is intended to include substances that can be coadministered with a multispecific molecule and allows the molecule to perform its intended function. Examples of such carriers include solutions, solvents, dispersion media, delay agents, emulsions and the like. The use of such media for pharmaceutically active substances are well known in the art, and are discussed infra. Any other conventional carrier suitable for use with the molecules falls within the scope of the instant invention. Further, therapy with the multispecific multivalent binding molecule may be coordinated into a treatment regimen with other similar molecules, or with traditional chemotherapeutic agents such as cis-platin, AZT, DDI, adriamyrin, tetracycline, cefachlor, nystatin, and acyclovir.

Combinatorial libraries can be screened to obtain members of the library with a desired binding activity, and to identify the active species, by methods that have been described (see, e.g., Gordon et al., *J Med. Chem.*, op. cit.). These include affinity chromatography with an appropriate "receptor" to isolate ligands for the receptor, followed by identification of the isolated ligands by conventional techniques (e.g., mass spectrometry and NMR). Preferably, the soluble receptor is conjugated to a label (e.g., fluorophores, calorimetric enzymes, radioisotopes, or luminescent compounds) that can be detected to indicate ligand binding. Alternatively, immobilized compounds can be selectively released and allowed to diffuse through a membrane to interact with a receptor.

Combinatorial libraries of compounds can also be synthesized with "tags" to encode the identity of each member of the library (see, e.g., W.C. Still et al., International Application WO 94/08051). In general, this method features the use of inert but readily detectable tags, that are attached to the solid support or to the compounds. When an active compound is detected the identity of the compound is determined by identification of the unique accompanying tag. This tagging method permits the synthesis of large libraries of compounds which can be identified at very low levels among to total set of all compounds in the library.

Specific binding proteins with high affinities for targets can be made according to methods known to those in the art. For example, proteins that bind specific DNA sequences may be engineered, and proteins that bind a variety of targets, especially protein targets (Ladner, R. C., et al., U.S. Pat. No. 5,233,409; Ladner, R. C., et al., U.S. Pat. No. 5,403,484) may be engineered and used in the present invention as the FcαR binding determinant or as the target binding determinant, as appropriate. Further, the methods of these libraries can be used in screens to obtain binding determinants that are mimetics of the structural determinants of antibodies.

In particular, the Fv binding surface of a particular antibody molecule interacts with its target ligand according to principles of protein-protein interactions, hence sequence data for $V_H$ and $V_L$ (the latter of which may be of the κ or λ chain type) is the basis for protein engineering techniques known to those with skill in the art. Details of the protein surface that comprises the binding determinants can be obtained from antibody sequence information, by a modeling procedure using previously determined three-dimensional structures from other antibodies obtained from NMR studies or crytallographic data. See for example Bajorath, J. and S. Sheriff, 1996, *Proteins. Struct., Funct., and Genet.* 24 (2), 152–157; Webster, D. M. and A. R. Rees, 1995, "Molecular modeling of antibody-combining sites," in S. Paul, Ed., *Methods in Molecular Biol.* 51, Antibody Engineering Protocols, Humana Press, Totowa, N.J., pp 17–49; and Johnson, G., Wu, T. T. and E. A. Kabat, 1995, "Seqhunt: A program to screen aligned nucleotide and amino acid sequences," in *Methods in Molecular Biol.* 51, op. cit., pp 1–15.

Breast and ovarian cancers are sex hormone dependent cancers. Breast tumors may be characterized by abnormally expressed receptors, e.g. those of the human-EGF-like receptor family (HER), for example HER-2, -3, and 4. The invention is not limited to these embodiments of HER antigens. The natural HER ligand, Heregulin, can be incorporated into a bispecific antibody (BsAb) or multispecific molecule, as a means to target a breast tumor cell expressing one or more HER receptor during cancer. Further, a heregulin molecules are binding determinants for heterodimeric HER receptors containing, eg. a monomer of each of HER-2, -3 or -4 in combination.

Additional examples of sex hormone-dependent cancer include prostate cancer (Smith, P. (1995), *Cancer Surveys Vol. 23: Preventing Prostate Cancer*, Imper. Cancer Research Fund and testicular cancers). The growth of hormone-dependent cancer types is promoted by male hormones (e.g., androgens such as testosterone and dihydrotestosterone). Removal of the testes (castration) was for many years the standard method of preventing secretion of male hormones by the gonads, to reduce growth of the cancer. Currently, secretion of male hormones is suppressed by chemical means by interfering with production of luteinizing hormone (LH), which regulates synthesis of male hormones. Similar considerations are applicable to other sex hormone-dependent cancers, such as breast or ovarian cancer, so that patients with these diseases or in a population prone to these diseases, are usually not administered sex hormones as therapeutic or replacements. Multispecific molecules of the invention can comprise binding determinants for sex hormones, to reduce the concentration and suppress tumor growth.

In a preferred embodiment, the methods of this invention include administration, for example, to a cancer patient, of a multi specific multivalent binding molecule preparation comprising at least one binding determinant with affinity for a tumor marker or a tumor-specific protein of the cancer to be treated, for example, the nestin protein for brain cancers. The nestin protein, which is expressed during normal mammalian fetal development, is also expressed on tumors of the central nervous system, including most forms of brain cancer (McKay, D. G. Ronald, U.S. Pat. No. 5,338,839, Aug. 16, 1994). It is also expressed on melanomas on the skin and on melanomas that have metastasized (V. A. Florenes, R. Holm, O. Myklebost, U. Lendahl, O. Fodstad, *Cancer Res.* 54: 354–6, 1994), to other organs and are difficult to detect and treat. The preferred site of delivery for treatment of a brain tumor with the molecules of this invention is directly into the central nervous system or directly, to the brain via spinal injection or fine needle delivery. For a metastatic cancer, a preferred delivery route would be by direct injection into the circulation, or by the ex vivo blood methods described herein.

Other tumor types for which the methods of this invention are exemplified by, but are not limited to, Wilm's tumor (A. J. Buckler, K. M. Call, T. M. Glaser, D. A. Haber, D. E. Housman, C. Y. Ito, J. Pelletier, Rose, E. A. Rose, U.S. Pat. No. 5,350,840) a pediatric kidney cancer due to occurrence of a somatic mutation in the patient's single copy of a gene normally found in two intact copies. Wilm's tumor can be cured surgically in 95% of cases, and a bispecific or multi-specific multivalent binding protein is envisioned to be suitable as an adjunct therapeutic modality for surgical patients. Other examples of known cancer-associated proteins for which the compositions of matter and methods of the current invention are suitable include those associated with gastrointestinal cancer (R. Fishel et al., International Application WO 95/14085, May 26, 1995), those characterized by development of multiple drug resistance during chemotherapy (J. M. Croop et al., U.S. Pat. No. 5,198,344), and a large number of oncogenes well known to the skilled artisan such as Rb, ras, and c-myc, the sequences of which are available for analysis to those with skill in the art. The compositions of this invention are, for example, suitable for inhibition of secreted enzymes such as matrix metalloproteinases, which are considered to potentiate tumor metastasis (Liotta, L. A., et al., (1991), *Cell*, 64: 327–336). In the latter embodiment, a multispecific binding molecule with a binding determinant to the matrix metalloproteinase and another for FcαR would facilitate inhibition and clearance of these enzymes from in situ activity. If used in conjunction with standard surgical and chemotherapeutic regimens, the compositions are foreseen to reduce cancer re-occurrence and enhance long-term survival.

IV. Pharmaceutical Compositions

The compounds of the invention can be incorporated into pharmaceutical compositions suitable for administration to a subject in vivo. In a preferred embodiment, the pharmaceutical composition comprises either a multispecific molecule (compound, or agent) of the invention and a pharmaceutically acceptable carrier. In yet another embodiment of the present invention, the pharmaceutical composition can be administered by combination therapy, i.e., combined with other agents. For example, the combination therapy can include a composition of the present invention with at least one anti-cancer agent, one antibiotic, one vaccine, or other conventional therapy. Exemplary anti-cancer agents include cis-platin, adriamycin, and taxol. Exemplary antibiotics include isoniazid, rifamycin, and tetracycline.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound may be coated in a material to protect the compound from the action of acids and other natural conditions that may inactivate the compound.

A "pharmaceutically acceptable salt" refers to a salt that retains the desired biological activity of the parent compound and does not impart any undesired toxicological effects (see e.g., Berge, S. M., et al. (1977) *J. Pharm. Sci.* 66: 1–19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A composition of the present invention can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., (1984) *J. Neuroimmunol.* 7: 27). Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporasterithe active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the therapeutic compositions, formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent.

Formulations of the present invention which are suitable for vaginal administration also include pessaries, tampons, creams, gels, pastes, foams or spray formulations containing such carriers as are known in the art to be appropriate. Dosage forms for the topical or transdermal administration of compositions of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

Transdermal patches offer the advantage of providing controlled delivery of a compound of the present therapeutic inventions to the body. Such dosage forms can be made by dissolving or dispersing the composition in the proper medium. Absorption enhancers can also be used to increase the flux of the composition across the skin. The rate of such flux can be controlled by either providing a rate controlling membrane or dispersing the composition in a polymer matrix or gel. Devices, including patches, which transdermally deliver a composition by iontophoresis or other electrically-assisted methods can also be employed in the present invention, including, for example, the devices described in U.S. Pat. Nos. 4,708,716 and 5,372,579.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

When the compounds of the present invention are administered as pharmaceuticals, to humans and animals, they can be given alone or as a pharmaceutical composition containing, for example, 0.01 to 99.5% (more preferably, 0.1 to 90%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of a compositions of the invention will be that amount of the compound which is the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of a therapeutic compositions may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical formulation (composition).

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in the present invention include: U.S. Pat. No. 4,487,603, which discloses an implantable microinfusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are well known to those skilled in the art.

In certain embodiments, the compounds of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29: 685). Exemplary targeting moieties include folate or biotin (see, e.g., U.S. Pat. No. 5,416,016 to Low et al.); mannosides (Umezawa et al., (1988) *Biochem. Biophys. Res. Commun.* 153: 1038); antibodies (P. G. Bloeman et al. (1995) *FEBS Lett.* 357: 140; M. Owais et al. (1995) *Antimicrob. Agents Chemother.* 39: 180); surfactant protein A receptor (Briscoe et al. (1995) *Am. J. Physiol.* 1233: 134), different species of which may comprise the formulations of the inventions, as well as components of the invented molecules; p120 (Schreier et al. (1994) *J. Biol. Chem.* 269: 9090); see also K. Keinanen; M. L. Laukkanen (1994) *FEBS Lett.* 346: 123; J. J. Killion; I. J. Fidler (1994) *Immunomethods* 4: 273. In one embodiment of the invention, the therapeutic compounds of the invention are formulated in liposomes; in a more preferred embodiment, the liposomes include a targeting moiety. In a most preferred embodiment, the therapeutic compounds in the liposomes are delivered by bolus injection to a site proximal to the tumor or infection. The composition must be fluid to the extent that easy syringability exists. It must be stable under the conditions of manufacture and storage and must be preserved against the contaminating action of microorganisms such as bacteria and fungi.

A "therapeutically effective dosage" preferably inhibits tumor growth or pathogen infection by at least about 20%, more preferably by at least about 40%, even more preferably by at least about 60%, and still more preferably by at least about 80% relative to untreated subjects. The ability of a compound to inhibit cancer or infectious disease can be evaluated in an animal model system predictive of efficacy in human tumors and infectious diseases. Alternatively, this property of a composition can be evaluated by examining the ability of the compound to inhibit, such inhibition in vitro by assays well-known to the skilled practitioner. A therapeutically effective amount of a therapeutic compound can decrease tumor size, prevent or delay death of infected tissues or organs, decrease fever and white cell count, improve CD4 count or otherwise ameliorate symptoms in a subject. One of ordinary skill in the art would be able to determine such amounts based on such factors as the subject's size, the severity of the subject's symptoms, and the particular composition or route of administration selected.

The composition must be sterile and fluid to the extent that the composition is deliverable by syringe. In addition to water, the carrier can be an isotonic buffered saline solution, ethanol, polyol (for example, glycerol, propylene glycol, and liquid polyetheylene glycol, and the like), and suitable mixtures thereof. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as manitol or sorbitol, and sodium chloride in the composition. Long-term absorption of the injectable compositions can be brought about by including in the composition an agent which delays absorption, for example, aluminum monostearate or gelatin.

When the active compound is suitably protected, as described above, the compound may be orally administered, for example, with an inert diluent or an assimilable edible carrier. As used herein "pharmaceutically acceptable carrier" includes any and all solvents, dispersion media, liposome formulations and coatings, antibacterial and antifungal agents, isotonic and absorption delaying agents, and other discussed above. The use of such media and agents for formulation of pharmaceutically active substances that are stable to oral administration is well known in the art. Except insofar as any conventional media or agent is incompatible with the active compound, use thereof in the therapeutic compositions is contemplated. Supplementary active compounds can also be incorporated into the compositions.

The invention is further illustrated by the following examples, which should not be construed as further limiting. The contents of all references, pending patent applications and published patents, cited throughout this application, are hereby expressly incorporated by reference.

EXAMPLES

The following methodology described in the Materials and Methods section was used throughout these Examples, set forth below.

Materials and Methods

Cell lines and Monoclonal antibodies

The murine hybridoma producing cell line for the anti-FcαR antibody is A77 (Monteiro et al. 1992, J. Immunol. 148: 1764–1770), and for the anti-HER2/neu antibody is 520C9 (Frankel, A. et al. 1995 J. Biol. Response Midifiers 4: 273–286; available from American Type Culture Collection, ATCC#HB 8696). Antibody H425 is a humanized anti-EGF-R antibody. SKBR-3 (Backman et al. Cancer Res 54: 2456–2461; available from American Type Culture Collection, ATCC, 12301 Parklawn Drive, Rockville, Md. 20852), a human breast carcinoma cell line which overexpresses the HER2/neu protooncogene, was cultivated in Iscove's Modified Dulbecco's Medium (IMDM, Gibco/BRL, Grand Island, N.Y.). The monocytoid cell line U937 (J. Immunol. 136: 1641–1647, 1986; ATCC) which expresses FcαR was grown in RPMI-1640 plus 10% FBS (Gibco/BRL, Grand Island, N.Y.).

The anti-FcαR mAb, A77, and the anti-HER2/neu mAb, 520C9, were purified from each respective hybridoma supernatant by protein A affinity chromatography (Bio-Rad, Richmond, Calif.) CC49 (anti-TAG 72 hybridoma) was obtained from the ATCC (#HB 9459).

Preparation of Blood Cells

Leukocytes were prepared from heparinized whole venous blood or from apheresis of normal human volunteers. Whole blood was diluted with RPMI containing 5% dextran at a ratio of 2.5:1 (v/v). The erythrocytes were allowed to sediment for 45 minutes on ice, then the cells in the supernatant were transferred to a new tube and pelleted by centrifugation. The residual erythrocytes were removed by hypotonic lysis. The remaining lymphocytes, monocytes and neutrophils were kept on ice until use in binding assays. For some experiments, neutrophils were separated from mononuclear cells by ficoll hypaque (Pharmacia-Upjohn, Piscataway, N.J.) gradient separation. Monocytes were enriched from mononuclear cells by cold aggregation and settling through a cushion of fetal calf serum. Monocyte cultures were used fresh or were incubated at 37° C., 5% $CO_2$ for 24 to 48 hours in teflon dishes at $4 \times 10^6$ cells/ml of MSFM containing 2.0% normal human serum type AB (Sigma, St. Louis, Mo.) and 500 IRU/ml IFN-γ (R&D Systems, Minneapolis, Minn.). Neutrophils were cultured for 24 to 48 hours (37° C., 5% $CO_2$) in AIM V media (Gibco/BRL, Grand Island, N.Y.) with 50 ng/ml G-CSF (Kindly provided by R. Repp, U. of Erlanger, Germany) and 500 IRU/ml IFN-γ.

Binding by flow cytometry

The binding of the BsAb to FcγR and HER2/neu was assessed by flow cytometry. Various concentrations of BsAb diluted in PBS, pH 7.4 containing 2 mg/ml BSA and 0.05% $NaN_3$ (PBA), were incubated with SKBR-3 cells or with human leukocytes for one hour at 0° C. The cells were washed with PBA and incubated with a phycoerythrin labeled goat anti-mouse antibody for one hour at 0° C. The cells were washed and fixed with 1% paraformaldehyde, and cell associated fluorescence was analyzed on a Becton Dickinson (Mountain View, Calif.) FACScan.

To assess whether IgA binding interfered with mAb A77 binding, A77 was incubated with TNF-treated cells in the presence of an excess of human IgA, and compared to controls incubated in the absence of IgA. A77 binding was detected with a phycoerythrin-labeled goat anti-mouse antibody as above. Cells were washed and fixed with 1% paraformaldehyde, and cell associated fluorescence was analyzed on a Becton Dickinson FACScan. In addition, binding human IgA to U937 cells was assessed in the presence of A77 mAb, and compared to controls in the absence of excess A77 mAb. IgA binding was detected with FITC labeled anti-human IgA antibody BsAb coupling procedure BsAb preparations were constructed using the method of Glennie et al. (J. Immunol. (1987) 139: 2367–2375). mAbs A77 (anti-FcαR), 520C9 (anti-HER2/neu), CC49 (anti-TAG 72) and H425 (anti-EGF-R) antibodies were produced by in vitro cultivation of the respective hybridoma cell lines. The antibody preparations were each digested with pepsin to produce $F(ab')_2$ preparations, and subsequently reduced to Fab' by addition of 10 mM mercaptoethanolamine (MEA) and incubation for 30 minutes at 30° C. The Fab' fragments were applied to a Sephadex G-25 (Pharmacia-Upjohn, Piscataway, N.J.) column equilibrated in 50 mM Na Acetate, 0.5 mM EDTA, pH 5.3 (4° C.). One-half volume of ortho-phenylenedimaleimide (o-PDM, 12 mM) dissolved in dimethylformamide and chilled in a methanol/ice bath was added to the 520C9 Fab', and the mixture was incubated 30 minutes at 0° C. The Fab'-maleimide was then separated from free o-PDM on Sephadex G-25 equilibrated in 50 mM Na Acetate, 0.5 mM EDTA, pH 5.3 (4° C.).

For preparation of BsAb, the 520C9 Fab'-maleimide was added to an equimolar solution of the A77 Fab'. The reactants were concentrated under nitrogen to the starting volume using a Diaflo membrane in an Amicon (Lexington, Mass.) chamber, at 4° C., for 18 hours. The pH was then adjusted to 8.0 with 1M Tris-HCl, pH 8.0, and the mixture was reduced with 10 mM MEA (30 minutes, 30° C.) and alkylated with 25 mM iodoacetamide. A77XCC49 and A77XH425 were produced using similar procedures. The bispecific $F(ab')_2$ reactant preparation was separated from unreacted Fab's and other materials using a Superdex 200 column (PharmaciaUpjohn, Piscataway, N.J.) equilibrated in PBS.

Antibody dependent cellular cytotoxicity (ADCC)

Human breast carcinoma cells, SKBR-3, which overexpress HER2/neu, were used as target cells for determination of lysis using multispecific compositions comprising binding determinants for HER2/neu. Other target cell lines were used in tests of molecules with different antigen-binding determinants, for example, A431 cells for EGF-R, KLEB for TAG 72, etc. Effector cell samples were obtained by using heparinized whole blood, purified neutrophils (purified as described previously, ref), or monocytes prepared from leukopaks obtained from Advanced Biotechnologies Inc. (Columbia, Md.) as previously described (Guyre, P. M. et al. 1989, *J Immunol.* 193: 1650). To prepare for use as effector cells, monocytes were cultured in Teflon containers in Macrophage Serum-Free Medium (Gibco/BRL) containing 2% human serum for 24 to 48 hours. Target cells were labeled with 100μ Ci of $^{51}Cr$ for one hour prior to combining with effector cells and antibodies in a U-bottom microtiter plate. After incubation for 16 to 18 hours at 37° C., supernatants from each well were collected and analyzed for radioactivity. Cytotoxicity was calculated by the formula: % lysis=(experimental CPM—target leak CPM/detergent lysis CPM—target leak CPM) X 100%. Further, specific lysis=% lysis with antibody −% lysis without antibody. Assays were performed in triplicate.

Fluoresceination of Antibodies

The pH of mAb solution was adjusted to 9.3 by the addition of 0.1M $Na_2CO_3$. Fluorescein iso-thiocyanate (FITC, Sigma, St. Louis, Mo.) was dissolved in DMSO at a concentration of 2 mg/ml. Forty μg of FITC was added for each milligram of mAb and incubated for two hours at room temperature. The fluoresceinated mAb was separated from the free FITC by G-25 chromatography.

Modulation of FcαR by mAb A 77

The ability of mAb A77 to modulate the number of FcαR on the surface of human monocytes was assessed by incubating monocytes with various dilutions of MAb A77 37° C. for 18 hours (or with mAb 520C9 as an isotype control). Monocytes were then washed with PBA, and incubated for one hour at 0° C. in the presence of human serum IgA at 100 μg/ml. Cells were further washed with PBA, and IgA binding to FcαR, was detected with FITC-labeled anti-human IgA antibody. Percent modulation=1−(MFI of the sample/MFI of the control)×100%, where MFI is the mean fluorescence intensity.

BsA b-mediated Phagocytosis

Assay of monocyte and neutrophil-mediated phagocytosis of SKBR-3 cells was performed with SKBR-3 target cells labeled with the lipophilic red fluorescent dye PKH 26. Buffy coat cells purified from heparinized whole blood containing monocytes, neutrophils, and lymphocytes were incubated with the labeled targets at 37° for 6 hours in the absence or presence of BsAb. Monocytes and neutrophils were stained with FITC labeled anti-CD14 mAb (AML-2-23) at 0° C., and cells were washed and analyzed by two color fluorescence by FACScan. Percent phagocytosis is expressed as the percent of effector cells (monocytes or neutrophils) that have PKH 26 stain associated with them.

Example 1

Bispecific Antibody A77X520C9 Binds Breast Cancer Cells and Mediates Cytolysis and Phagocytosis To determine efficacy of the bispecific antibody BsAb A77X520C9 in killing breast cancer cells in a patient, ability to specifically bind to breast cancer cells in culture was determined. For these experiments, cells of line SKBR-3, which overexpresses the HER2/neu oncogene, were used. The 520C9 binding determinant derives from an anti-HER2/neu murine hybridoma (Ring et al. 1991 J. Immunol. 28: 915–917).

Figure 2:
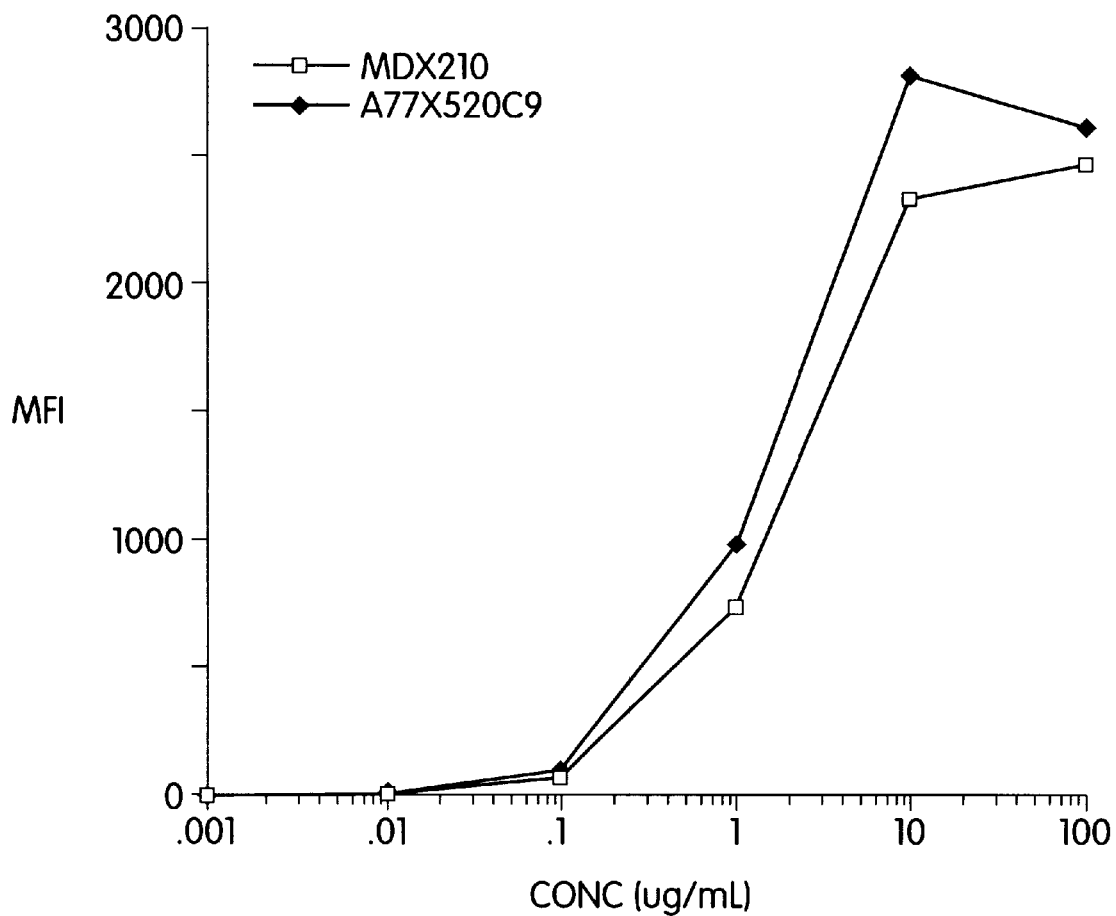
FIG. 2 is a graph showing the extent of binding of A77×520C9, the anti-FcαR×anti-HER2/neu BsAb, as a function of concentration in micrograms per milliliter, to SKBR3 breast tumor cells, in which mean fluorescence intensity analyzed by FACScan is the measure of binding.

FIG. 1 shows that BsAb A77X520C9 bound to each of two types of effector cells, neutrophils (PMN) and monocytes. Further the data in FIG. 2 show that the BsAb A77X520C9 bound to breast tumor cells as well as the previously described BsAb MBX210 (Valone et al. 1995 J. Clin. Oncol. 13(9): 2281–2292). Mean fluorescence intensity (MFI) as a measure of binding was found to increase as a function of BsAb concentration when breast tumor cells were incubated with each of 0.1, 1.0 or 10 micrograms per milliliter. Fraction of A77X520C9 BsAb bound to tumor cells was equivalent to or greater than to the control BsAb MDX210, (FIG. 2) and the binding function to effector cells (FIG. 1) was similar as a function of concentration of the BsAb.

Figure 3:
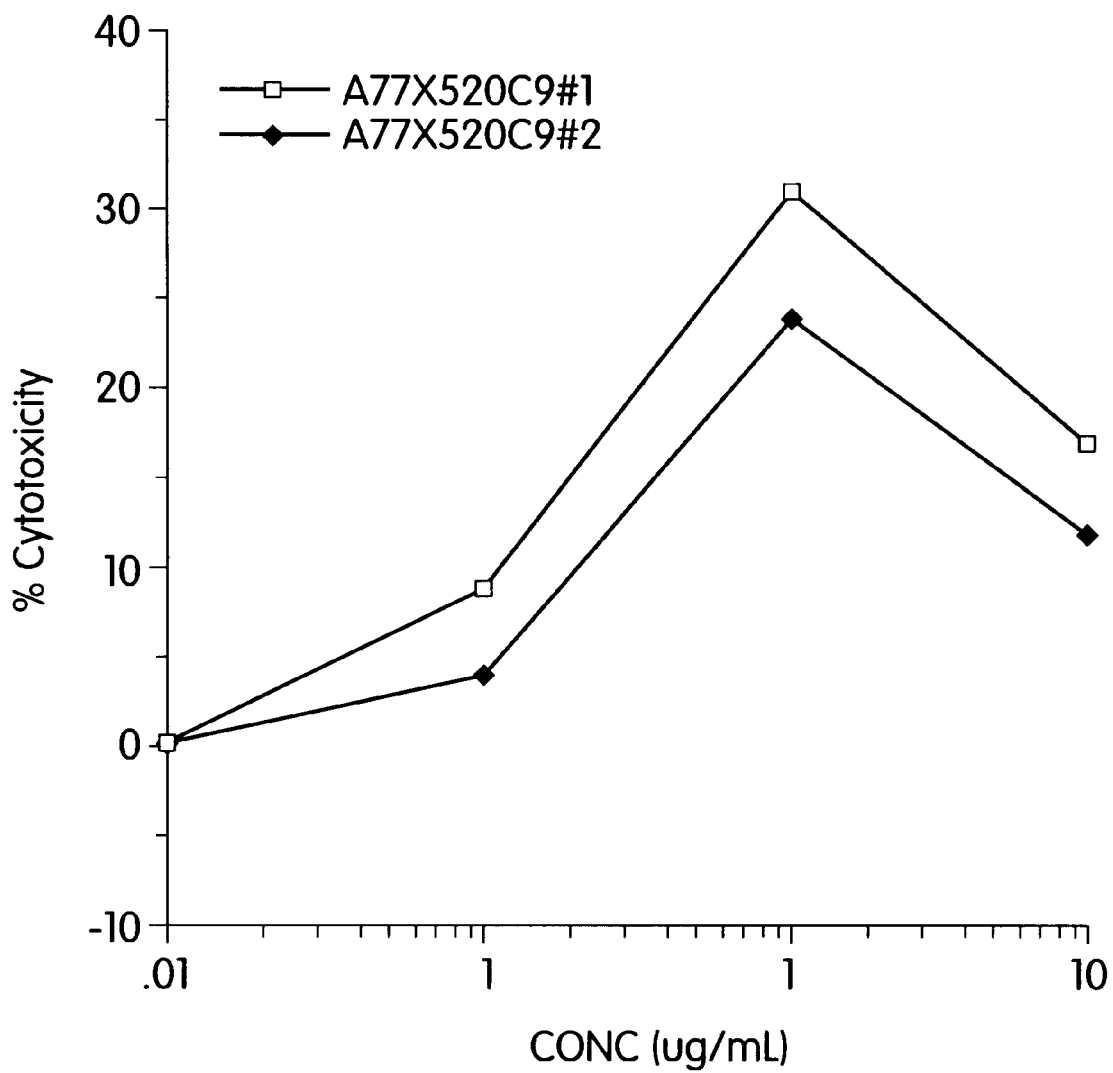
FIG. 3 is a graph showing the extent of BsAb-mediated killing, as a function of concentration in micrograms per milliliter, of breast tumor cells by unstimulated neutrophils, at a ratio of effector to target cells of 200 to one.

Following determination of binding of A77X520C9 to breast tumor cells, another aspect of BsAb functionality, ability to bind to specific leukocytes such that cytolysis of the breast tumor cells is effected, was determined and is shown in FIG. 3, with varying concentrations of two different preparations of BsAb. Cytotoxicity mediated by A77X520C9 varied from 6% to 9% at 0.1 micrograms per milliliter, and increased to 20% to 30% at 1.0 microgram per milliliter.

Figure 4:
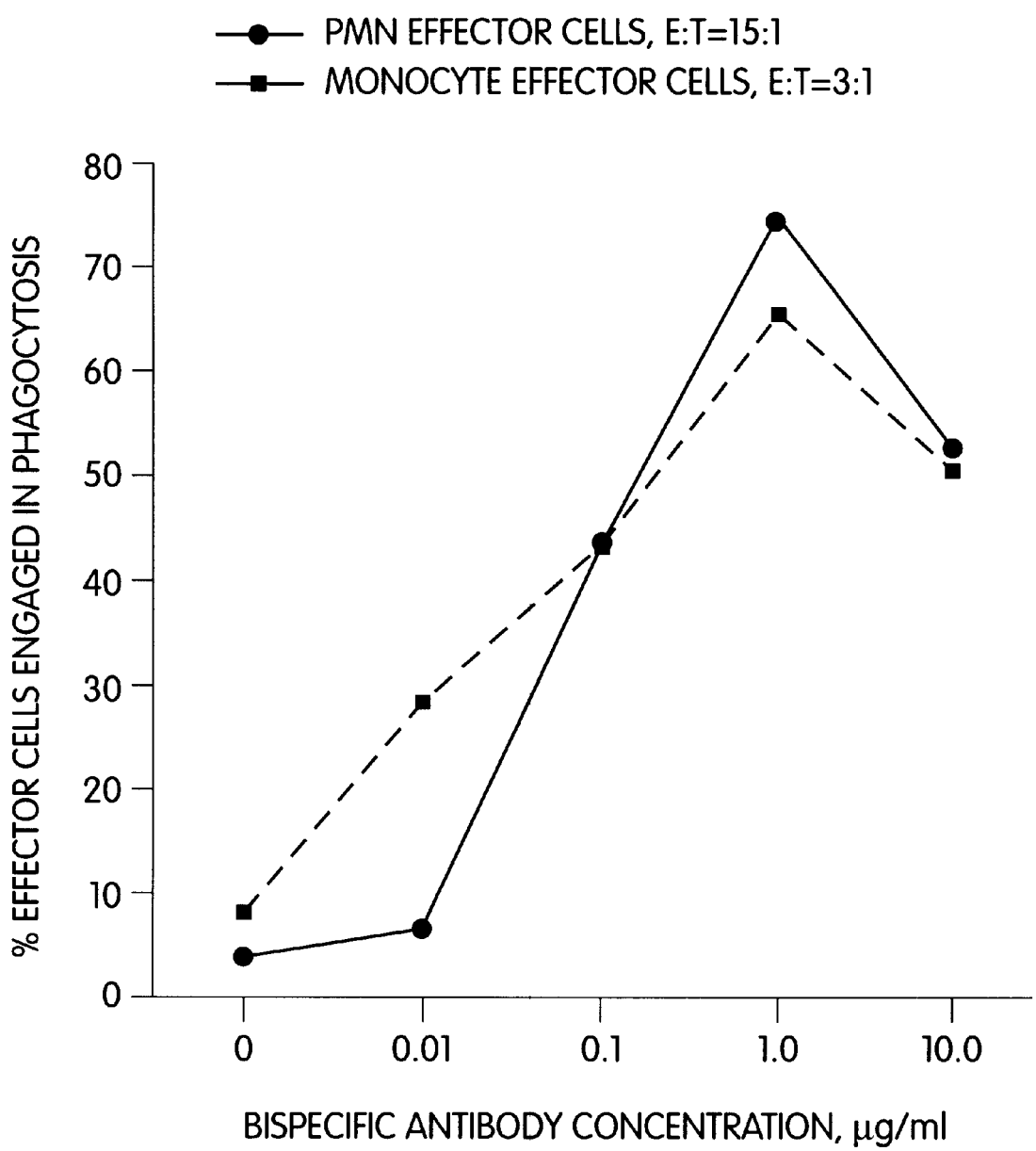
FIG. 4 is a graph showing the extent of BsAb-mediated phagocytosis, as a function of concentration in micrograms per milliliter, of breast tumor cells at a ratio of 15 neutrophils per target cell, and 3 monocytes per target cell.

Another measure of functionality of the BsAb is mediation of phagocytosis, so experiments were performed to determine the extent to which effector cells engulf the breast tumor cells in the presence of BsAb A77X529. In the procedure used here, tumor cells were labeled prior to exposure to leukocytes with a lipophilic red fluorescent dye PKH26. Following incubation of effector cells with target cells for 6 hours, effector monocytes and neutrophils purified from whole blood were stained with FITC-labeled anti-CD14 mAb, and were analyzed by cell sorting. Percent phagocytosis is expressed as FITC-stained effector cells associated with the lipophilic red dye. As shown in FIG. 4, percent effector cells engaged in phagocytosis was on the order of 65% to 75%, depending on whether monocytes or neutrophils were tested. Increasing the bispecific antibody concentration above 1.0 microgram per milliliter did not enhance the percent of effector cells engaged in phagocytosis.

The data in FIGS. 1, 2, 3 and 4 show that the BsAb A77X520C9 bound both effector and target cells, mediated cytolysis and directed neutrophil and monocyte phagocytosis of breast tumor cells.

Example 2

Figure 5A:
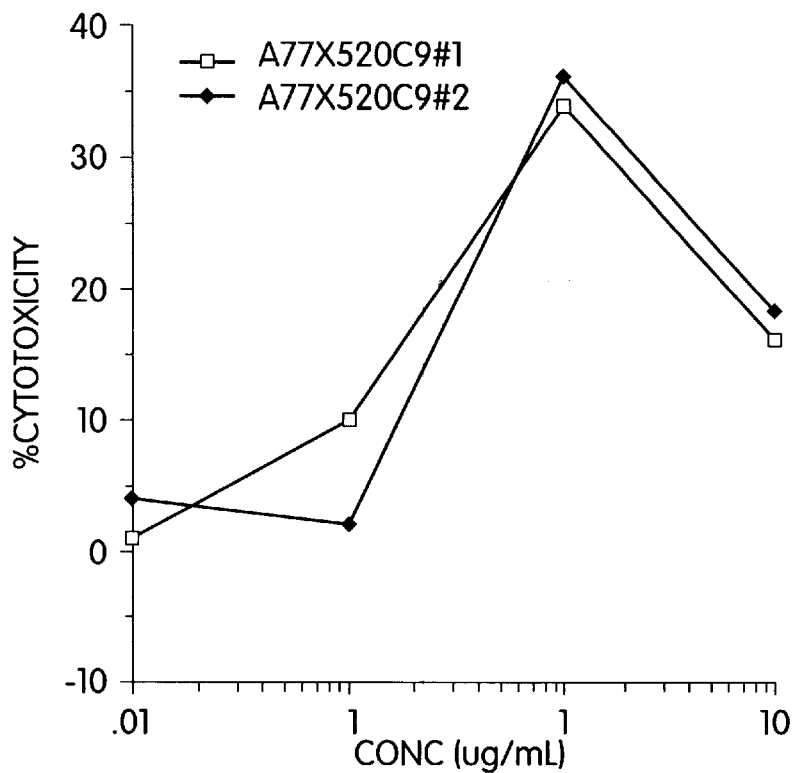
FIG. 5 is a graph showing the extent of BsAb-mediated killing, as a function of concentration in micrograms per milliliter, of breast tumor cells by neutrophils treated with G-CSF (Panel A), and with G-CSF, or with IFN-γ (Panel B).
Figure 5B:
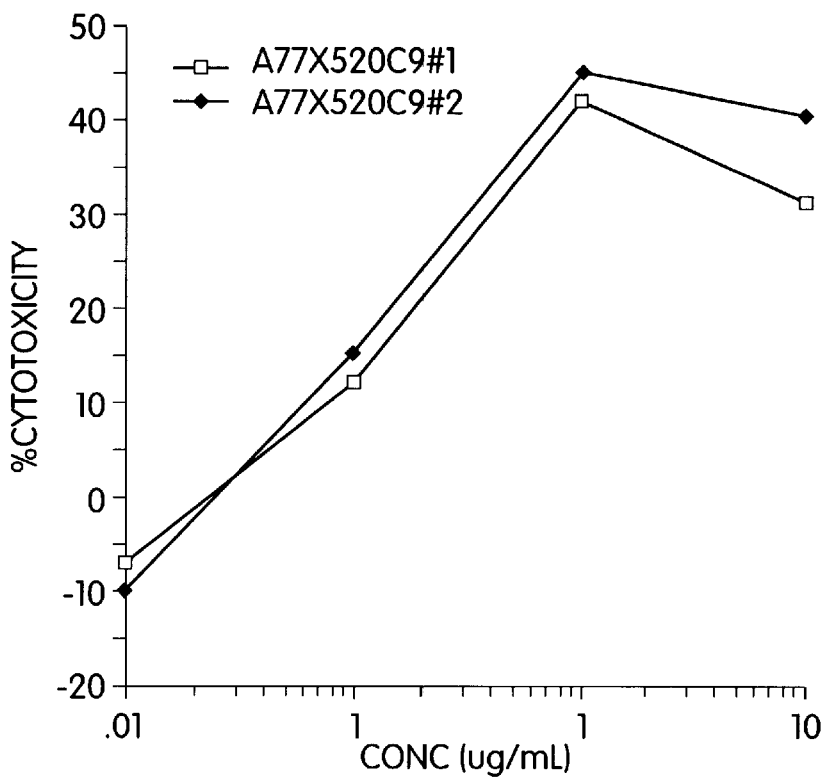

BsAb-Mediated Cytolysis With Effector Cells Treated With Cytokines and Growth Factors FIG. 5 shows percent cytotoxicity as a function of concentration of the bispecific antibody, as in the previous example, using effector cells pre-incubated with G-CSF (Panel A) or both G-CSF and IFN-γ (Panel B). Cells were pre-incubated with these factors overnight at 37° prior to the cytotoxicity assay. In comparison with data in Example 1, percent cytotoxicity was found to be enhanced by pre-incubation of effector cells with both G-CSF and IFN-γ, such that at 0.1 microgram per milliliter BsAb, greater than 10% of tumor cells were specifically lysed compared to less than 10% seen in Example 1, and at 1.0 microgram per milliliter BsAb, greater than 40% cytotoxicity was observed compared to approximately 24% to 32% in FIG. 3 in the absence of these factors.

Figure 6A:
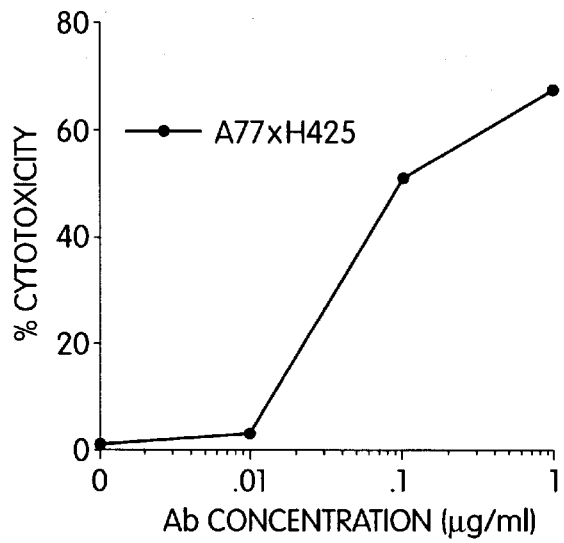
FIG. 6 is a graph showing the extent of BsAb-mediated killing, as a function of concentration in micrograms per milliliter, of breast tumor cells by IFN-γ-treated monocytes (Panel B), by TNF-treated monocytes (Panel C), or by untreated monocytes (Panel A).
Figure 6B:
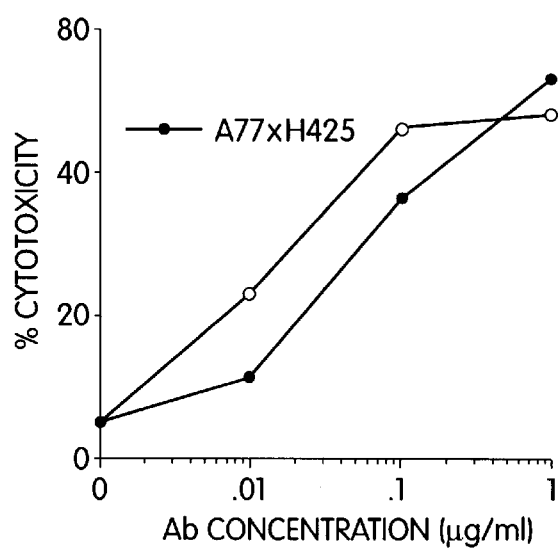
Figure 6C:
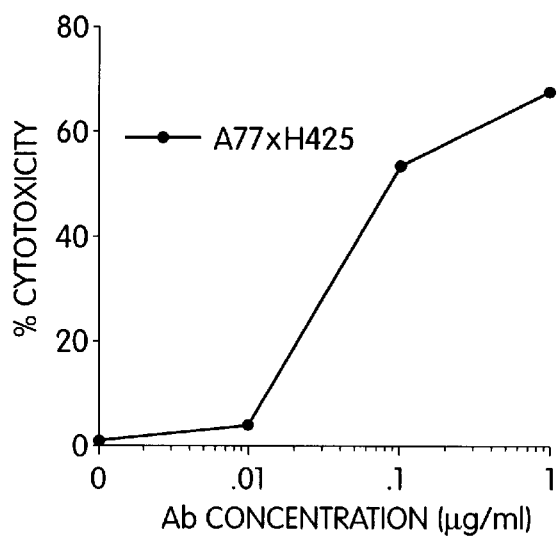

FIG. 6 shows the results of pre-treating effector monocytes with IFN-γ(Panel B) or TNF (Panel C), using BsAb A77XH425, which combines the binding determinant for FcαR with the binding determinant for EGF-R. As described above, EGF receptors are known to be overexpressed on breast and other tumor cells, so that BsAb A77XH425 comprises another embodiment of a multispecific composition for treatment of breast and other tumors. The data show that monocytes caused substantial breast cancer cell cytotoxicity following treatment with A77XH425 BsAb without addition of other factors, at BsAb concentrations of 0.1 microgram per milliliter and 1.0 microgram per milliliter. Specifically, BsAb A77XH425 caused greater than 60% cytolysis at 1.0 microgram per milliliter with untreated monocytes and with TNF treated monocytes, and greater than 40% at 1.0 microgram per milliliter with IFN-γ-treated monocytes.

Thus each of the two BsAb preparations, A77X520C9 and A77XH425, were found to bind to breast tumor cells and to mediate cytolysis of the cancer cells by neutrophils or monocytes without additional treatment.

Example 3

Figure 7:
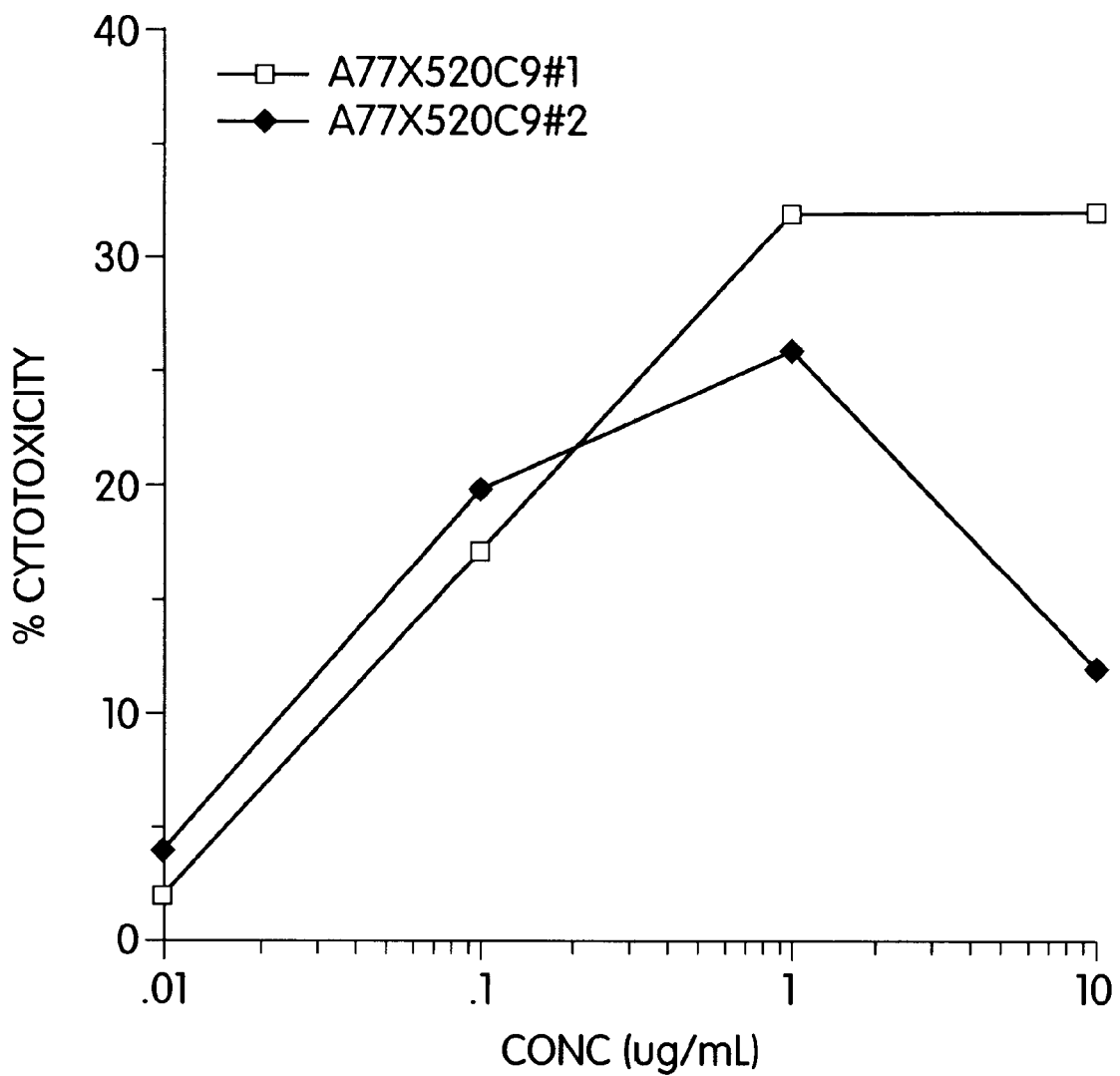
FIG. 7 is a graph showing the extent of BsAb-mediated killing, as a function of concentration in micrograms per milliliter, of breast tumor cells by effector cells in whole blood.

The Effect of BsAb A77X520C9 on Cytotoxicity Mediated by Effector Cells in Whole Blood Therapy of subjects with multispecific multivalent chemical compositions directly administered into the circulation requires that these agents function in whole blood. Ability to function in whole blood was analyzed by the experiment shown in FIG. 7, in which A77X520C9 preparations were found to mediate cytolysis of cultured breast tumor cells by blood effector cells. At 0.1 microgram per milliliter, between 15% and 20% of the tumor cells were lysed by A77X520C9, and at 1.0 microgram per milliliter cytolysis was approximately 25% to 30% of breast tumor cells. Since whole blood contains IgA at a concentration of 2 to 5 mg/ml, these data also show that cytotoxic activity of this BsAb is not inhibited by IgA. These results show that BsAb can be delivered for therapeutic application in vivo.

Example 4

BsAb Cytolysis Requires Access to FcαR Via the A77 Binding Determinant Moiety

Figure 8:
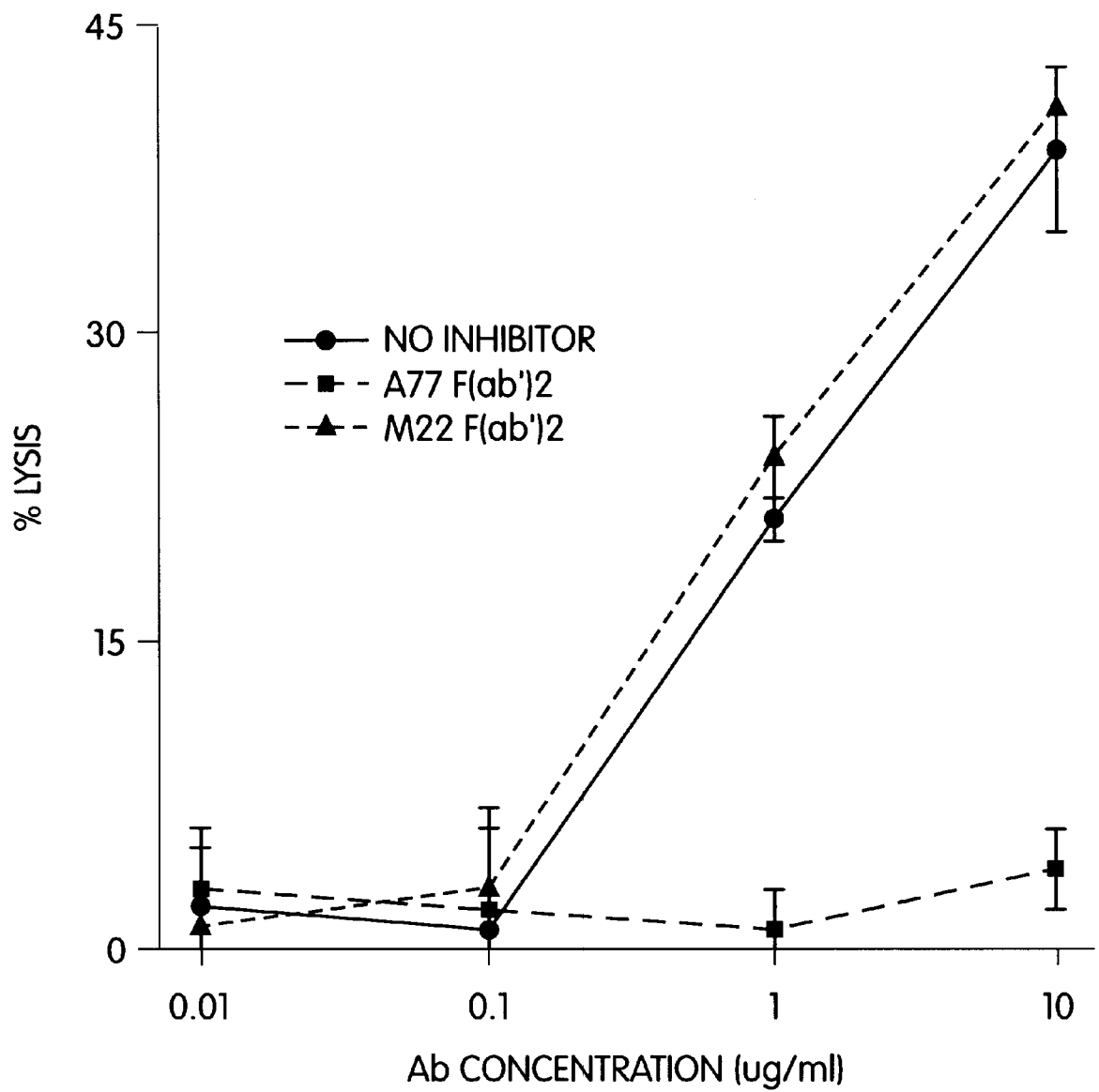
FIG. 8 is a graph showing the extent of inhibition of BsAb-mediated whole blood killing, as a function of concentration in micrograms per milliliter, by anti-FcαR F(ab')$_2$ (50 micrograms per milliliter), compared to addition of 50 micrograms per milliliter anti-FcγR M77 F(ab')$_2$ and no addition of inhibitor as controls.

To show that BsAb-mediated cytolysis of breast tumor cells is due to FcαR recognition by the A77 binding determinant, A77XH425 cytolysis was analyzed in the presence of A77 F(ab')$_2$. If BsAb-mediated cytolysis functions by binding to FcαR because of the A77-derived binding determinant, then the addition of A77 F(ab')$_2$, but not an antibody with a different receptor binding determinant, could cause inhibition of cytolysis of breast tumor cells. In FIG. 8, A77XH425-mediated cytolysis of tumor cells by whole blood is observed at 1.0 microgram per milliliter and 10 micrograms per milliliter in the absence of additional antibody (closed circles), similar to level of cytolysis found with untreated monocytes (FIG. 6, Panel A).

Figure 9:
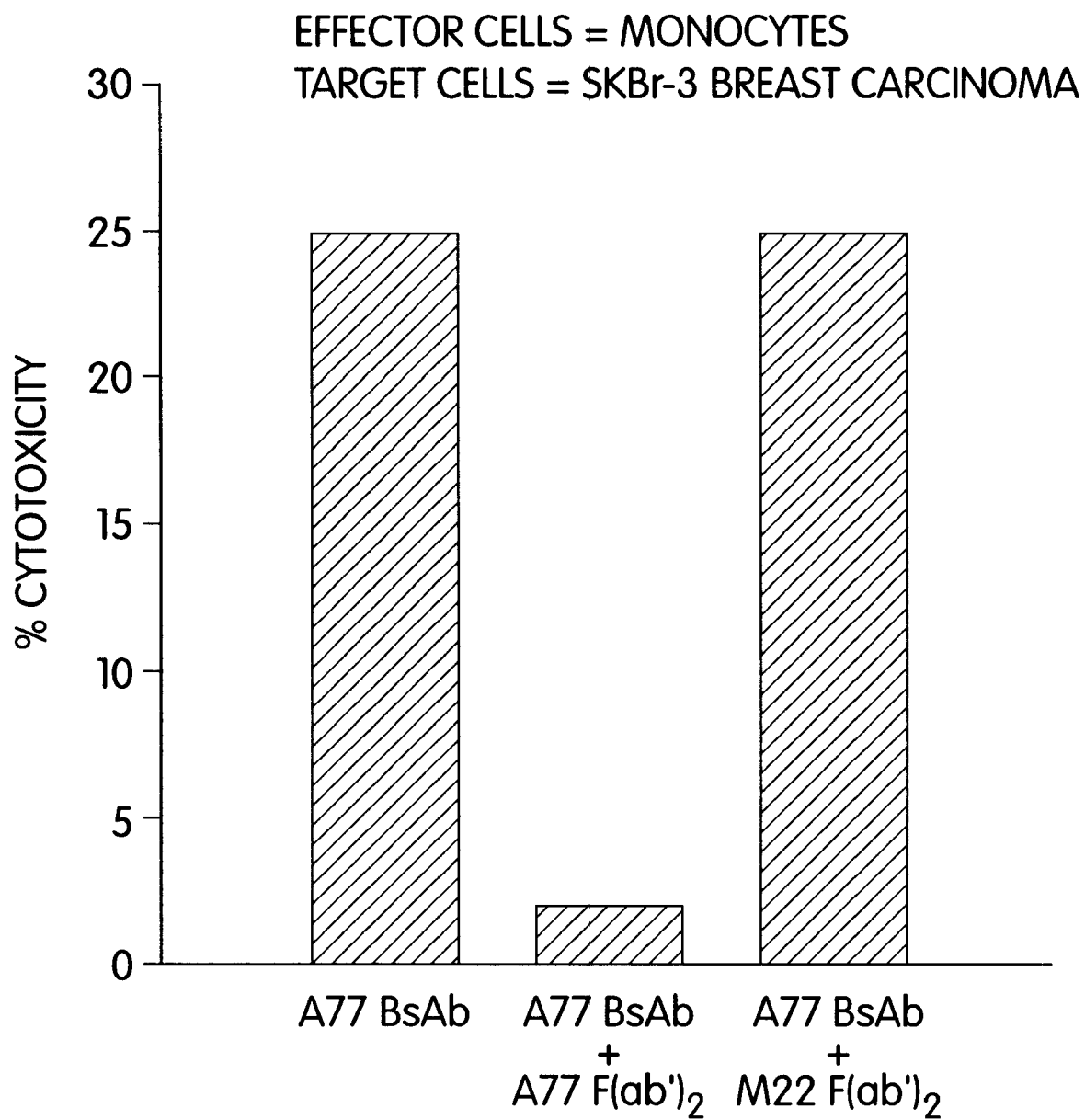
FIG. 9 is a bar graph showing specificity of inhibition by anti-FcαR A77 F(ab')$_2$ of BsAb-mediated killing of breast tumor cells by monocytes, compared to addition of anti-FcγR M22 F(ab')$_2$ and no additions as controls.

Inhibition was observed in the presence 50 micrograms/ml A77 F(ab')$_2$, and not in the presence of 50 micrograms/ml of M22 F(ab')$_2$. M22 F(ab')$_2$ specifically binds a different receptor, the FcγRI receptor (Valone et al., 1995 J. Clin. Oncol. 13: 2281–2292). These data show that A77XH425-mediated cytolysis of tumor cells depends on specific binding of the BsAb to FcαR on effector cells. Similar inhibition of BsAb killing by A77 F(ab')$_2$ was found using monocytes as effector cell (FIG. 9).

Example 5

The A77 FcαR Binding Site is Different From That of FcαR for its Natural Ligand

Figure 10:
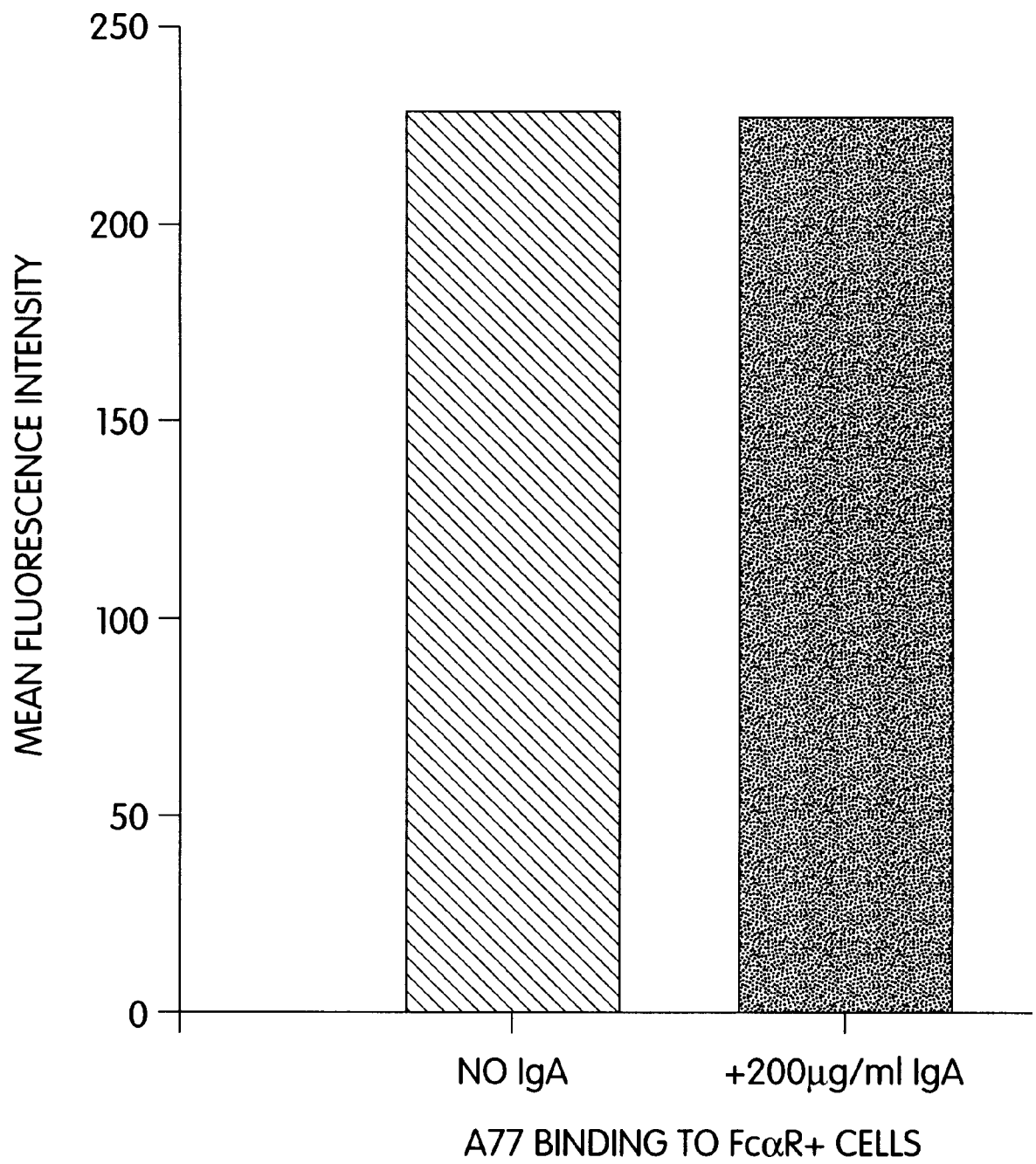
FIG. 10 is a bar graph showing that pre-incubation of effector cells with human IgA does not inhibit binding of A77 mAb.

In design of a therapeutic BsAb directed to FcocR, optimal functionality as a therapeutic agent in subjects would be achieved if binding of this entity were independent of competition with endogenous molecular species, in particular, binding of the natural ligand IgA. FIG. 10 shows that A77 antibody bound to the full extent to effector cells in the presence of IgA at 200 micrograms per milliliter, compared to control binding in the absence of IgA. Mean fluorescence intensity was unaffected by the presence of IgA. The A77 mAb specifically binds an epitope on FcαR that is different from the site for binding of IgA (Monteiro et al. 1992, *J. Immunol.* 148: 1764–1770).

Example 6

FcαR Modulation by A77 in Monocytes

Figure 11:
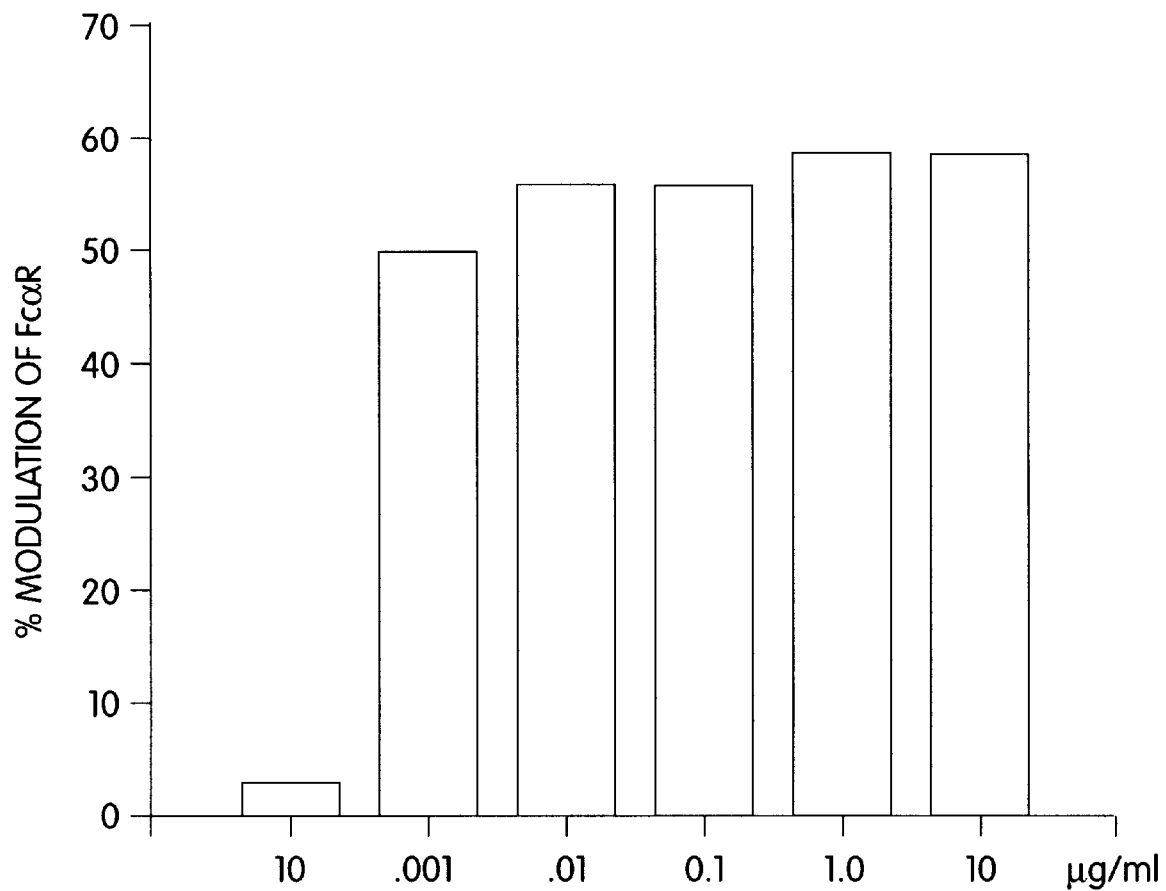
FIG. 11 is a bar graph showing modulation of Fcα receptors by treatment with A77 mAb at concentrations ranging from 0.001 to 10 micrograms per milliliter, showing decreased number of cell surface receptors with increasing A77.

Characterization of the effect of addition of A77 mAb to cells on FcαR regulation is shown in the experiment of FIG. 11, in which modulation (decrease in receptor number) of FcαR from the cell surface was examined as a function of concentration of A77 mAb.

Incubation of monocytes with various concentrations of A77 for 18 h at 37° C. caused modulation at 10 nanograms per milliliter, which reached a plateau at 55% to 60% of control (number of receptors in the absence of A77 ) at 1.0 to 10 micrograms per milliliter. In contrast, incubation of monocytes with antibody 520C9, which has the same isotype as A77 and which specifically binds the HER2/neu receptor that is not expressed on monocytes, had no effect on monocyte modulation of FcαR. Thus the A77 mab functional determinant is capable of causing internalization and modulation of FcαR from the surface. Further, ability of the BsAb to bind HER2/neu by virtue of a binding determinant derived from 520C9 is independent of the FcαR binding determinant. This result shows that down modulation of FcαR is achieved by incubation of cells bearing this receptor with antibody A77. Such modulation can be used for regulation of autoimmune disorders.

Example 7

Figure 12:
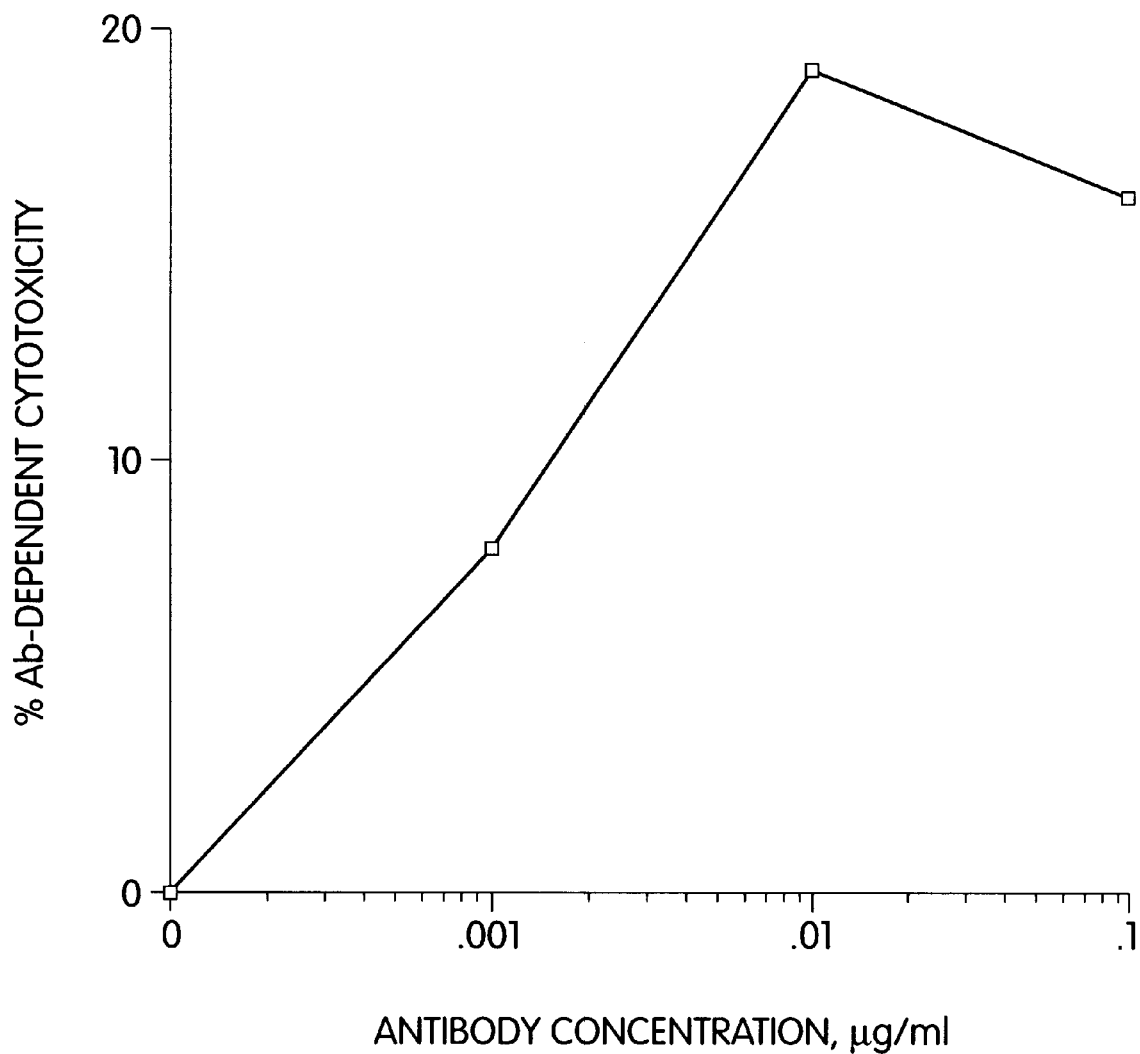
FIG. 12 is a graph showing Anti-TAG 72×A77 BsAb-mediated killing by unstimulated neutrophils of TAG 72 bearing tumor cells, as a function of antibody concentration in micrograms per milliliter.

Bispecific Antibody anti-TAG 72×A77 Mediates Cytolysis of TAG 72 Bearing Tumor Cells FIG. 12 illustrates another bispecific antibody embodiment of the invention for therapeutic application to a cancer antigen, the mucine antigen TAG 72 found in the majority of breast, colon, ovarian and other cancers. A variety of antibodies that specifically bind TAG 72 are available, for example CC49 (ATCC HB 9459, Mezes, P. et al., International Application WO 90/04410). CC49 was coupled to A77 to produce BsAb anti-TAG72XA77, to target tumor cells bearing the TAG72 antigen specifically to effector cells bearing FcαR.

FIG. 12 shows antibody-dependent cytotoxicity by the BsAb anti-TAG 72×A77 (constructed from CC49 and A77 antibodies) of TAG 72-bearing tumor cells, as a function of concentration in micrograms per milliliter. The data show that BsAb anti-TAG 72×A77 mediated cytolysis of tumor cells to a similar extent as BsAbs A77X520C9 (FIG. 3) and A77XH425 (FIG. 6).

Example 8

Stimulation of T-cell Growth by Antigen-Presentation Using a Bispecific Antibody For use of a bispecific molecule for delivery of an antigen, the following procedure was used for coupling of mAb A77 to tetanus toxoid. Purified tetanus toxoid (TT, Accurate Chemical and Scientific Company, Westbury, N.Y.) was reacted with sulfo-succidimidyl, 4-(N-maleimidomethyl) cyclohexane-1-carboxylate (s-SMCC, Pierce, Rockford, Ill.) at a molar ratio of 20 SMMC: 1 TT for two hours at room temperature. Free SMCC was removed from TT:SMCC by G-25 chromatography. The F(ab')2 fragment of mAb, A77, was reduced to Fab' by incubating in the presence of 5 mM mercaptoethylamine (MEA, Sigma, St. Louis, Mo.) for 30 minutes at 30° C. Free MEA was removed from Fab' by G-25 chromatography. The A77 Fab' was incubated with the SMCC-treated TT for two hours at room temperature followed by an overnight incubation at 4° C. The A77 -TT conjugate was purified from uncoupled Fab' by Superdex 200 gel filtration (Pharmacia-Upjohn, Piscataway, N.J.).

To assay T cell proliferation following antigen presentation, TT-specific T cell lines were generated from immunized individuals as previously described (Gosselin, E. J. et al. *J. Immunol.* 179:3477, 1992), monocytes were purified by cold aggregation as described previously (Guyre, P. M. et al. *J. Immunol.* 143:1650, 1989) and T cells (50 µl of $10^6$/ml) and autologous monocytes (50 µl of $5 \times 10^5$/ml) were added to wells of a 96 well tissue culture plate in the presence of various concentrations of TT or of A77 -TT and incubated at 37° in a $CO_2$ incubator. The relative number of T cells in each well was assessed after incubation for four days by measuring lactate dehydrogenase (LDH) released from cells after lysis using a kit purchased from Promega (Madison, Wis.). LDH levels were quantified spectrophotometrically after addition of substrate and stop solution. Optical density was read at 490 nm using an ELISA plate reader (Molecular Devices, Palo Alto, Calif.).

Figure 13:
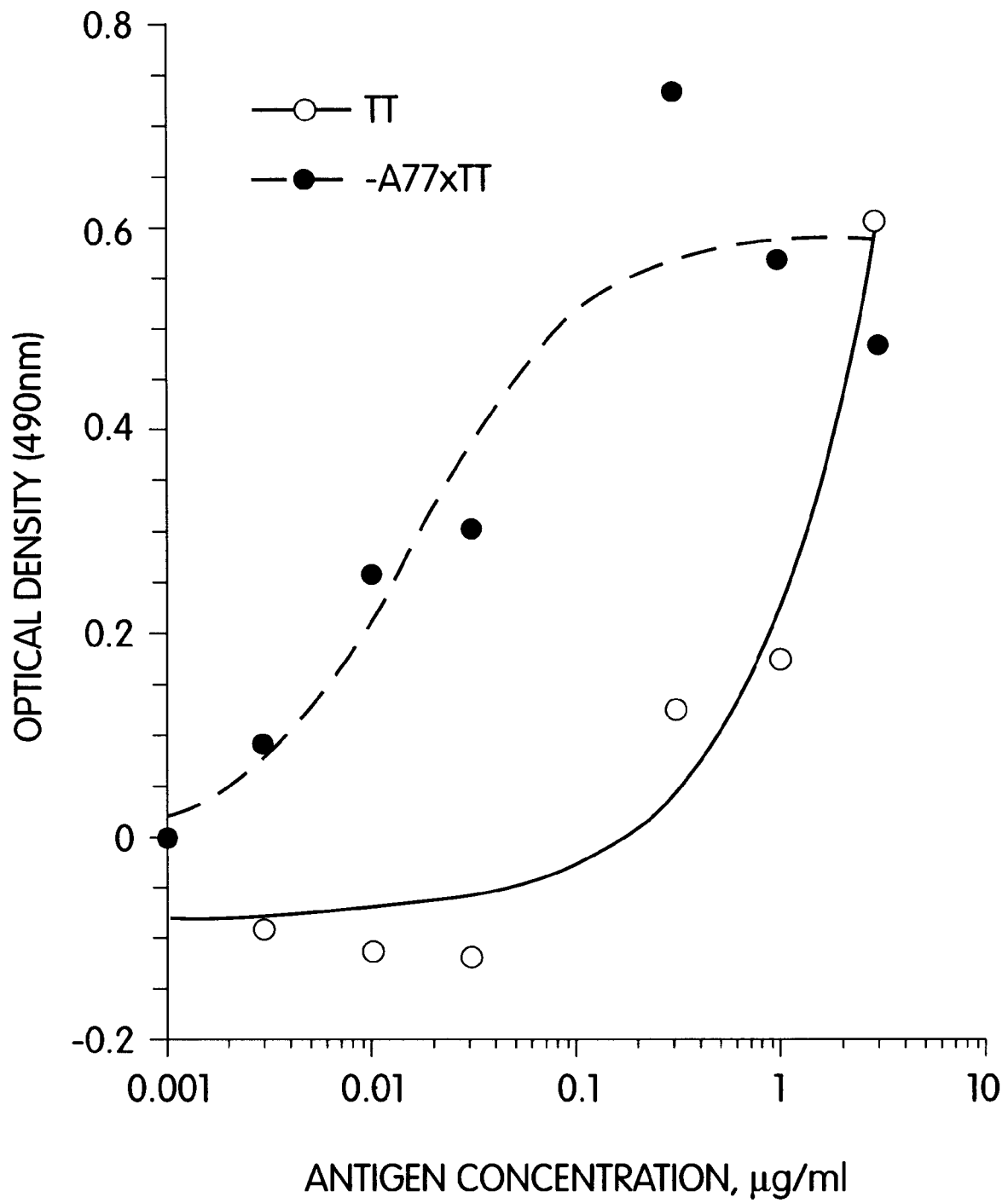
FIG. 13 is a graph showing relative stimulation of growth of tetanus toxoid (TT) -specific T cells by monocyte presentation of this antigen by A77-linked TT and by TT alone, as a function of concentration of each antigen in micrograms per milliliter, measured by total cellular lactate dehydrogenase.

Each data point presented in FIG. 13 is the mean of data obtained from quadruplicate samples, with background value (monocytes and T cells in the presence of media only) subtracted. The A77-TT conjugate induced equivalent T cell proliferation at antigen doses that were 30–100 fold lower than that of the uncoupled TT. These data show that directing the TT antigen to FcαcR by coupling to mAb A77 clearly enhanced monocyte presentation of TT to TT-specific T cells.

Example 9

Cloning and Sequencing A77 Variable Region Genes

A77 RNA was prepared from A77 FcαR specific antibody producing hybridoma cells, and 33 µg of total RNA was obtained from approximately $4 \times 10^7$ A77 cells using the RNAeasy Total RNA kit (Qiagen). RT-PCR was then done on 200 ng of the total RNA preparation using the GeneAmp Thermostable rTth Reverse Transcriptase RNA PCR kit (Perkin Elmer). Ig V region cDNAs were made using primers CG1FOR, 5'-GGAAGCTTAGACAGATGGGGGTGTCGTTTTG (encoding amino acids 115–122 of the murine IgG1 heavy chain CH1 domain and a HindIII site; SEQ ID NO: 1) and CK2FOR, 5'GGAAGCTTGAAGATGGATACAGTTGGTGCAGC (encoding amino acids 111–118 of the murine κ light chain constant domain and a HindIII site; SEQ ID NO: 2).

The $V_H$ and $V_K$ cDNAs were amplified by PCR using the cDNA primers along with SH1BACKBAM, 5'- GACTGGA TCCATGGRATGGAGCTGGRTCWTBHTCTT (encoding a consensus sequence of amino acids −20 to −12 of some $V_H$ signal peptides and a BamHI site; SEQ ID NO: 3) and VK1BACKBAM, 5'GACTGGATCCGACATTCAGCT- GACCCAGTCTCCA (encoding amino acids −4 to −1 of the signal peptide and residues 1 to 4 of some murine $V_\kappa$ domains and a BamHI site; SEQ ID NO: 4). The single-letter code for combinations of nucleotides, known to those of skill in the art, is given on p. 174 of the 1996–1997 New England Biolabs catalog (32 Tozer Rd., Beverly, Mass.).

Amplified $V_H$ and $V_\kappa$ DNA were purified using Wizard PCR Prep kit (Promega), cloned into pUC19, and sequenced by the dideoxy method. DNA sequencing was carried out by National Biosciences, Inc. At least 5 pUC 19 clones of each $V_\kappa$ and $V_H$ were sequenced to obtain consensus sequences of these genes, which are shown in FIGS. 14 (SEQ ID NO: 5) and 15 (SEQ ID NO: 7). The predicted amino acid sequences are shown in FIGS. 14 (SEQ ID NO: 6) and 15 (SEQ ID NO: 8) for $V_\kappa$ and $V_H$ respectively.

These sequences are used to obtain recombinant humanized A77 Fcα R-binding determinants, to produce single-chain antibodies and single-chain BsAbs, for engineering determinants with greater affinity using recombinant methods, for modeling studies to develop mimetic drugs using rational drug design, and for additional applications described in the instant invention.

Equivalents

Those skilled in the art will recognize, or be able to ascertain using no more than routine experimentation, many equivalents to the specific embodiments of the invention described herein. Such equivalents are intended to be encompassed by the following claims.

The contents of all patents and publications referred to herein are hereby incorporated by reference.

What is claimed is:

1. A bispecific molecule, comprising a first binding determinant which is an antibody or an antigen binding fragment thereof which binds to an Fcα receptor without being blocked by immunoglobulin A, and a second binding determinant which binds to a target antigen.

2. The bispecific molecule of claim 1, wherein the targer antigen is a cancer cell antigen.

3. The bispecific molecule of claim 1, wherein the cancer cell is selected from the group consisting of cells from cancers of the breast, ovary, testis, lung, colon, rectum, pancreas, liver, central nervous system, head and neck, kidney, bone, blood and lymphatic system.

4. The bispecific molecule of claim 1, wherein the target antigen is an antigen from a pathogen or pathogen-infected cell.

5. The bispecific molecule of claim 2, wherein the cancer cell antigen is a member of the human EGF-like receptor family.

6. The bispecific molecule of claim 5, wherein the cancer cell antigen is an EGF receptor.

7. The bispecific molecule of claim 5, wherein the cancer cell antigen is HER2/neu.

8. The bispecific molecule of claim 5, wherein the cancer cell antigen is selected from the group consisting of HER-3, HER-4, and a heterodimeric receptor comprised of at least one HER subunit.

9. The bispecific molecule of claim 2, wherein the cancer cell antigen is selected from the group consisting of carcinoembryonic antigen, gastrin releasing peptide receptor antigen, and mucine tumor antigen TAG 72.

10. The bispecific molecule of claim 1, wherein at least one of said first and second binding determinants comprises an antibody or an antigen binding fragment thereof.

11. The bispecific molecule of claim 10, wherein the antibody is an IgG.

12. The bispecific molecule of claim 10, wherein the antigen binding fragment is selected from the group consisting of an Fab, Fab', F(ab')$_2$, Fv, and single chain Fv.

13. A bispecific molecule, comprising: (a) a fragment of antibody A77 which binds to an Fcα receptor without being blocked by immunoglobulin A; and (b) a binding determinant which binds to a cancer cell antigen or a pathogen antigen.

14. The bispecific molecule of claim 13, wherein the fragment of antibody A77 is a humanized fragment.

15. The bispecific binding molecule of claim 14, wherein the humanized fragment is encoded by all or a portion of the nucleotide sequences encoding the Fv binding determinants of antibody A77 $V_\kappa$ and $V_H$ regions shown in FIG. 14 (SEQ ID NO:5), and FIG. 15 (SEQ ID NO:7), respectively.

16. The bispecific molecule of claim 14, wherein the humanized fragment corresponds to all or a portion of the amino acid residue sequences of the Fv binding determinants of antibody A77 $V_\kappa$ and $V_H$ regions shown in FIG. 14 (SEQ ID NO:6), and FIG. 15 (SEQ ID NO:8), respectively.

17. The bispecific molecule of claim 13, wherein said binding determinant which binds a cancer cell antigen comprises a functional fragment of antibody 520C9 specific for HER-2/neu (ATCC #HB 8696) or antibody CC49 specific for TAG 72 (ATCC #HB 9459).

18. The bispecific molecule of claim 17, produced by chemical linkage of said binding determinants.

19. The bispecific molecule of claim 17, produced recombinantly.

20. The bispecific molecule of claim 19, wherein said binding determinants are encoded by genes which are reconbinantly linked.

21. The bispecific molecule of claim 17, produced by fusion of cell lines carrying one or more nucleic acids encoding said binding determinants.

22. The bispecific molecule of claim 1, wherein said second binding determinant comprises a ligand.

23. The bispecific molecule of claim 22, wherein the ligand binds to a tumor cell.

24. A bispecific molecule, comprising a binding determinant which is an antibody or an antigen binding fragment thereof, which binds to an Fcα receptor without being blocked by IgA, and an antigen.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 31 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: misc_feature
      (B) LOCATION: 1..31
      (D) OTHER INFORMATION: /note= "PCR primer"

(xi) SEQUENCE DESCRIPTION: SEQ ID NO:1:

GGAAGCTTAG ACAGATGGGG GTGTCGTTTT G                              31

(2) INFORMATION FOR SEQ ID NO:2:

(i) SEQUENCE CHARACTERISTICS:
      (A) LENGTH: 32 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: misc_feature
      (B) LOCATION: 1..32
      (D) OTHER INFORMATION: /note= "PCR primer"

(xi) SEQUENCE DESCRIPTION: SEQ ID NO:2:

GGAAGCTTGA AGATGGATAC AGTTGGTGCA GC                            32

(2) INFORMATION FOR SEQ ID NO:3:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (ii) MOLECULE TYPE: cDNA (vi) FEATURE:
            (A) NAME/KEY: misc_feature
            (B) LOCATION: 1..36
            (D) OTHER INFORMATION: /note= "PCR primer"

(vii) FEATURE:
            (A) NAME/KEY: misc_feature
            (B) LOCATION: 15,26
            (D) OTHER INFORMATION: /note= "R is A or G"

(viii) FEATURE:
            (A) NAME/KEY: misc_feature
            (B) LOCATION: 29
            (D) OTHER INFORMATION: /note= "W is A or T"

(ix) FEATURE:
            (A) NAME/KEY: misc_feature
            (B) LOCATION: 31
            (D) OTHER INFORMATION: /note= "B is C or G or T"

(x) FEATURE:
            (A) NAME/KEY: misc_feature
            (B) LOCATION: 32
            (D) OTHER INFORMATION: /note= "H is A or C or T"

(xi) SEQUENCE DESCRIPTION: SEQ ID NO:3:

GACTGGATCC ATGGRATGGA GCTGGRTCWT BHTCTT                                36

(2) INFORMATION FOR SEQ ID NO:4:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: misc_feature
            (B) LOCATION: 1..34
            (D) OTHER INFORMATION: /note= "PCR primer"

(xi) SEQUENCE DESCRIPTION: SEQ ID NO:4:

GACTGGATCC GACATTCAGC TGACCCAGTC TCCA                                  34

(2) INFORMATION FOR SEQ ID NO:5:

(i) SEQUENCE CHARACTERISTICS:
            (A) LENGTH: 336 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: CDS
            (B) LOCATION: 1..336

(xi) SEQUENCE DESCRIPTION: SEQ ID NO:5:

```
GAC ATT CAG CTG ACC CAG TCT CCA CTC ACT TTG TCG ATT ACC ATT GGA        48
Asp Ile Gln Leu Thr Gln Ser Pro Leu Thr Leu Ser Ile Thr Ile Gly
 1               5                  10                  15

CAA CCA GCC TCC ATC TCT TGC AAG TCA AGT CAG AGC CTC TTA GAT AGT        96
Gln Pro Ala Ser Ile Ser Cys Lys Ser Ser Gln Ser Leu Leu Asp Ser
                20                  25                  30

GAT GGA AAG ACA TAT TTG AAT TGG TTG TTA CAG AGG CCA GGC CAG TCT       144
Asp Gly Lys Thr Tyr Leu Asn Trp Leu Leu Gln Arg Pro Gly Gln Ser
            35                  40                  45

CCA ACG CGC CTA ATC TAT CTG GTG TCT AAA CTG GAC TCT GGA GTC CCT       192
```

```
                            -continued

Pro Thr Arg Leu Ile Tyr Leu Val Ser Lys Leu Asp Ser Gly Val Pro
     50                  55                  60

GAC AGG TTC ACT GGC AGT GGA TCA GGG ACA GAT TTC ACA CTG AAA ATC      240
Asp Arg Phe Thr Gly Ser Gly Ser Gly Thr Asp Phe Thr Leu Lys Ile
 65                  70                  75                  80

AGC AGA GTG GAG GCT GAG GAT TTG GGA ATT TAT TAT TGC TGG CAA GGT      288
Ser Arg Val Glu Ala Glu Asp Leu Gly Ile Tyr Tyr Cys Trp Gln Gly
                 85                  90                  95

GCA CAT TTT CCT CAG ACG TTC GGT GGA GGC ACC AAG CTG GAA ATC AAA      336
Ala His Phe Pro Gln Thr Phe Gly Gly Gly Thr Lys Leu Glu Ile Lys
            100                 105                 110

(2) INFORMATION FOR SEQ ID NO:6:

(i) SEQUENCE CHARACTERISTICS:
        (A) LENGTH: 112 amino acids
        (B) TYPE: amino acid
        (D) TOPOLOGY: linear (ii) MOLECULE TYPE: peptide (xi) SEQUENCE DESCRIPTION: SEQ ID NO:6:

Asp Ile Gln Leu Thr Gln Ser Pro Leu Thr Leu Ser Ile Thr Ile Gly
 1               5                  10                  15

Gln Pro Ala Ser Ile Ser Cys Lys Ser Ser Gln Ser Leu Leu Asp Ser
                 20                  25                  30

Asp Gly Lys Thr Tyr Leu Asn Trp Leu Leu Gln Arg Pro Gly Gln Ser
             35                  40                  45

Pro Thr Arg Leu Ile Tyr Leu Val Ser Lys Leu Asp Ser Gly Val Pro
     50                  55                  60

Asp Arg Phe Thr Gly Ser Gly Ser Gly Thr Asp Phe Thr Leu Lys Ile
 65                  70                  75                  80

Ser Arg Val Glu Ala Glu Asp Leu Gly Ile Tyr Tyr Cys Trp Gln Gly
                 85                  90                  95

Ala His Phe Pro Gln Thr Phe Gly Gly Gly Thr Lys Leu Glu Ile Lys
            100                 105                 110

(2) INFORMATION FOR SEQ ID NO:7:

(i) SEQUENCE CHARACTERISTICS:
        (A) LENGTH: 426 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..426

(xi) SEQUENCE DESCRIPTION: SEQ ID NO:7:

ATG GGA TGG AGC TGG GTC ATT ATC TTC CTC CTG TCA GGA ACT GCA GGA       48
Met Gly Trp Ser Trp Val Ile Ile Phe Leu Leu Ser Gly Thr Ala Gly
 1               5                  10                  15

GCC CAC TCT GAG ATC CAG CTG CAG CAG ACT GGA CCT GAG CTG GTG AAG       96
Ala His Ser Glu Ile Gln Leu Gln Gln Thr Gly Pro Glu Leu Val Lys
                 20                  25                  30

CCT GGG GCT TCA GTG AAG ATA TCC TGC AAG GCT TCT GGT TAT TCA TTC      144
Pro Gly Ala Ser Val Lys Ile Ser Cys Lys Ala Ser Gly Tyr Ser Phe
             35                  40                  45

ACT GAC TAC ATC ATA TTT TGG GTG AAG CAG AGC CAT GGA AAG AGC CTT      192
Thr Asp Tyr Ile Ile Phe Trp Val Lys Gln Ser His Gly Lys Ser Leu
     50                  55                  60
```

```
GAG TGG ACT GGA AAT ATT AAT CCT TAC TAT GGT AGT ACT AGC TAC AAT        240
Glu Trp Thr Gly Asn Ile Asn Pro Tyr Tyr Gly Ser Thr Ser Tyr Asn
 65                  70                  75                  80

CTG AAG TTC AAG GGC AAG GCC ACA TTG ACT GTA GAC AAA TCT TCC AGC        288
Leu Lys Phe Lys Gly Lys Ala Thr Leu Thr Val Asp Lys Ser Ser Ser
                 85                  90                  95

ACA GCC TAC ATG CAG CTC AAC AGT CTG ACA TCT GAG GAC TCT GCA GTC        336
Thr Ala Tyr Met Gln Leu Asn Ser Leu Thr Ser Glu Asp Ser Ala Val
                100                 105                 110

TAT TAC TGT GTA AGA GGA GTT TAT TAC TAC GGT AGT AGC TAC GAG GCG        384
Tyr Tyr Cys Val Arg Gly Val Tyr Tyr Tyr Gly Ser Ser Tyr Glu Ala
            115                 120                 125

TTT CCT TAC TGG GGC CAA GGG ACT CTG GTC ACT GTC TCT GCA                426
Phe Pro Tyr Trp Gly Gln Gly Thr Leu Val Thr Val Ser Ala
130                 135                 140
```

(2) INFORMATION FOR SEQ ID NO:8:

(i) SEQUENCE CHARACTERISTICS:
        (A) LENGTH: 142 amino acids
        (B) TYPE: amino acid
        (D) TOPOLOGY: linear (ii) MOLECULE TYPE: peptide (xi) SEQUENCE DESCRIPTION: SEQ ID NO:8:

```
Met Gly Trp Ser Trp Val Ile Ile Phe Leu Leu Ser Gly Thr Ala Gly
 1               5                  10                  15

Ala His Ser Glu Ile Gln Leu Gln Gln Thr Gly Pro Glu Leu Val Lys
                 20                  25                  30

Pro Gly Ala Ser Val Lys Ile Ser Cys Lys Ala Ser Gly Tyr Ser Phe
             35                  40                  45

Thr Asp Tyr Ile Ile Phe Trp Val Lys Gln Ser His Gly Lys Ser Leu
         50                  55                  60

Glu Trp Thr Gly Asn Ile Asn Pro Tyr Tyr Gly Ser Thr Ser Tyr Asn
 65                  70                  75                  80

Leu Lys Phe Lys Gly Lys Ala Thr Leu Thr Val Asp Lys Ser Ser Ser
                 85                  90                  95

Thr Ala Tyr Met Gln Leu Asn Ser Leu Thr Ser Glu Asp Ser Ala Val
                100                 105                 110

Tyr Tyr Cys Val Arg Gly Val Tyr Tyr Tyr Gly Ser Ser Tyr Glu Ala
            115                 120                 125

Phe Pro Tyr Trp Gly Gln Gly Thr Leu Val Thr Val Ser Ala
130                 135                 140
```